United States Patent
Bruce et al.

(10) Patent No.: US 11,723,633 B2
(45) Date of Patent: Aug. 15, 2023

(54) BIOPSY DEVICE WITH SELF-REVERSING CUTTER DRIVE

(71) Applicant: Devicor Medical Products, Inc., Cincinnati, OH (US)

(72) Inventors: John Kevin Bruce, Burlington, KY (US); Mark Graham, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1047 days.

(21) Appl. No.: 16/509,878

(22) Filed: Jul. 12, 2019

(65) Prior Publication Data

US 2020/0015795 A1    Jan. 16, 2020

Related U.S. Application Data

(60) Provisional application No. 62/697,430, filed on Jul. 13, 2018.

(51) Int. Cl.
*A61B 10/02* (2006.01)
*F16C 1/02* (2006.01)

(52) U.S. Cl.
CPC ............ *A61B 10/0275* (2013.01); *F16C 1/02* (2013.01)

(58) Field of Classification Search
CPC .......... A61B 10/00–06; A61B 10/0275; A61B 90/00; A61B 90/11; A61B 17/34; A61B 10/66; A61B 10/0283; A61B 10/0291; A61B 17/3205–32053; A61B 2010/045; A61B 2017/320064; F16C 1/02
See application file for complete search history.

(56) References Cited

U.S. PATENT DOCUMENTS

| | | | |
|---|---|---|---|
| 5,526,822 A | 6/1996 | Burbank et al. |
| 5,928,164 A | 7/1999 | Burbank et al. |
| 6,017,316 A | 1/2000 | Ritchart et al. |
| 6,086,544 A | 7/2000 | Hibner et al. |
| 6,162,187 A | 12/2000 | Buzzard et al. |
| 6,432,065 B1 | 8/2002 | Burdorff et al. |
| 6,626,849 B2 | 9/2003 | Huitema et al. |
| 6,752,768 B2 | 6/2004 | Burdorff et al. |

(Continued)

FOREIGN PATENT DOCUMENTS

| | | | | |
|---|---|---|---|---|
| JP | 2006198401 | * | 8/2006 | |
| WO | WO-2010107424 A1 | * | 9/2010 | ......... A61B 10/0275 |
| WO | WO-2016053742 A1 | * | 4/2016 | ......... A61B 10/0266 |

OTHER PUBLICATIONS

Machine Translation of JP 2006198401, Patent Translate, 17 pages, printed on Aug. 31, 2022 (Year: 2006).*

(Continued)

*Primary Examiner* — Matthew Kremer
*Assistant Examiner* — Om Patel
(74) *Attorney, Agent, or Firm* — Frost Brown Todd LLP

(57) ABSTRACT

A biopsy device includes a body, a needle, a cutter, and a cutter drive mechanism. The needle extends distally from the body. The cutter is movable relative to the needle to sever a tissue sample. The cutter drive mechanism is driven by a rotary drive cable and is configured to both rotate and translate the cutter. The cutter drive mechanism is further configured to reverse the transition direction of the cutter wile the drive provided by the rotary drive cable is in a continuous rotary direction.

13 Claims, 27 Drawing Sheets

(56) References Cited

U.S. PATENT DOCUMENTS

| | | |
|---|---|---|
| 7,442,171 B2 | 10/2008 | Stephens et al. |
| 7,507,210 B2 | 3/2009 | Hibner et al. |
| 7,648,466 B2 | 1/2010 | Stephens et al. |
| 7,831,290 B2 | 11/2010 | Hughes et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,454,531 B2 | 6/2013 | Speeg et al. |
| 8,568,333 B2 | 10/2013 | Hibner et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,923,233 B2 | 12/2014 | Ko et al. |
| 8,938,285 B2 | 1/2015 | Fiebig et al. |
| 8,968,212 B2 | 3/2015 | Speeg et al. |
| 9,095,326 B2 | 8/2015 | Ritchie et al. |
| 9,119,609 B2 * | 9/2015 | O'Sullivan ............ A61B 10/02 |
| 9,326,755 B2 | 5/2016 | Fiebig et al. |
| 9,345,457 B2 | 5/2016 | Speeg et al. |
| 9,638,770 B2 | 5/2017 | Dietz et al. |
| 9,931,104 B2 | 4/2018 | Rhad et al. |
| 2006/0074345 A1 | 4/2006 | Hibner |
| 2009/0131821 A1 | 5/2009 | Speeg et al. |
| 2010/0152610 A1 | 6/2010 | Parihar et al. |
| 2010/0160817 A1 * | 6/2010 | Dahling ............. A61B 10/0283 600/565 |
| 2010/0160819 A1 | 6/2010 | Parihar et al. |
| 2010/0292607 A1 * | 11/2010 | Moore ............... A61B 10/0266 600/566 |
| 2012/0065542 A1 | 3/2012 | Hibner et al. |
| 2013/0079665 A1 * | 3/2013 | Hibner ............... A61B 10/0275 600/567 |
| 2013/0324882 A1 | 12/2013 | Mescher |

OTHER PUBLICATIONS

International Search Report and Written Opinion dated Aug. 17, 2016 for Application No. PCT/US2016/036659, 8 pages.

* cited by examiner

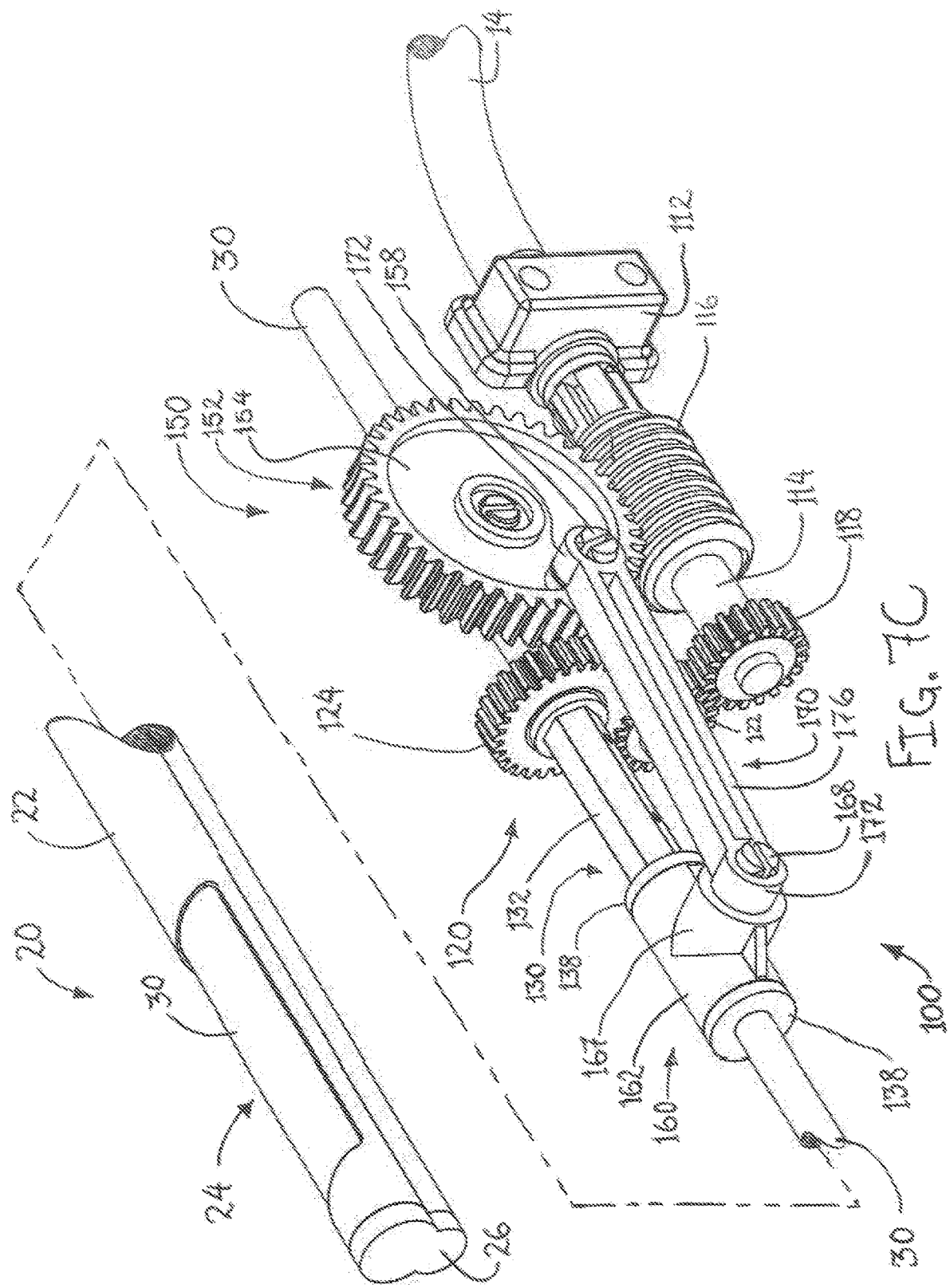

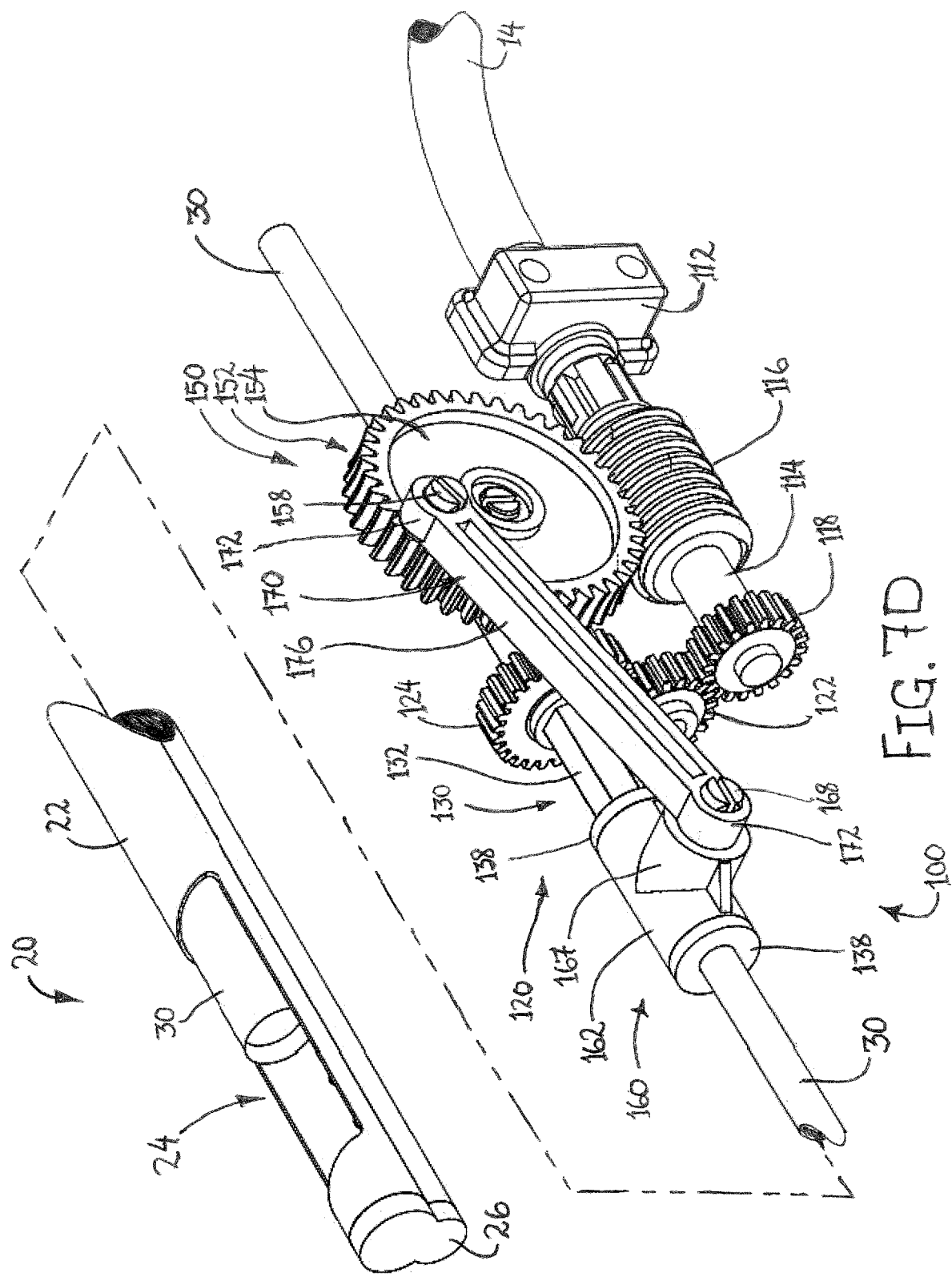

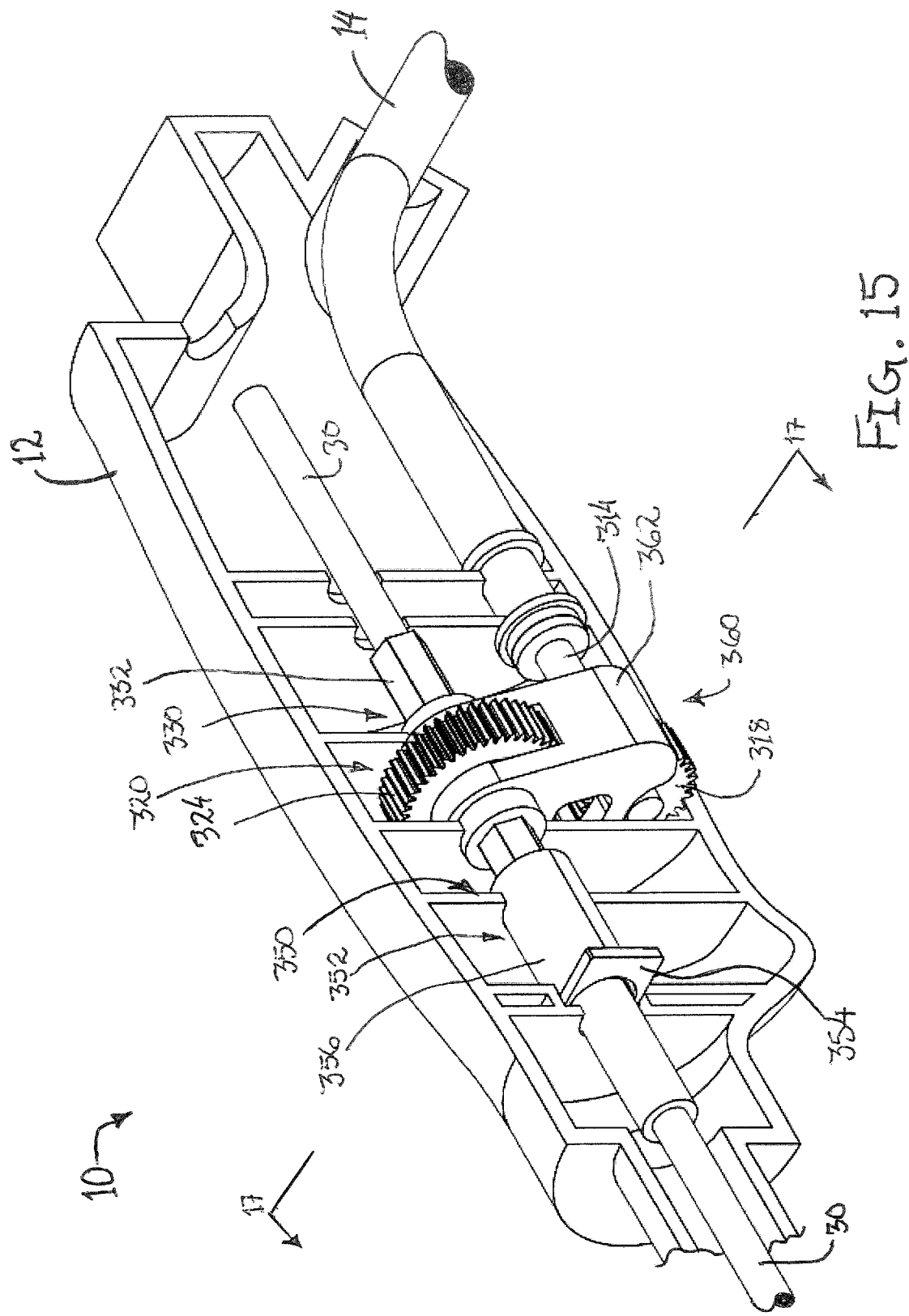

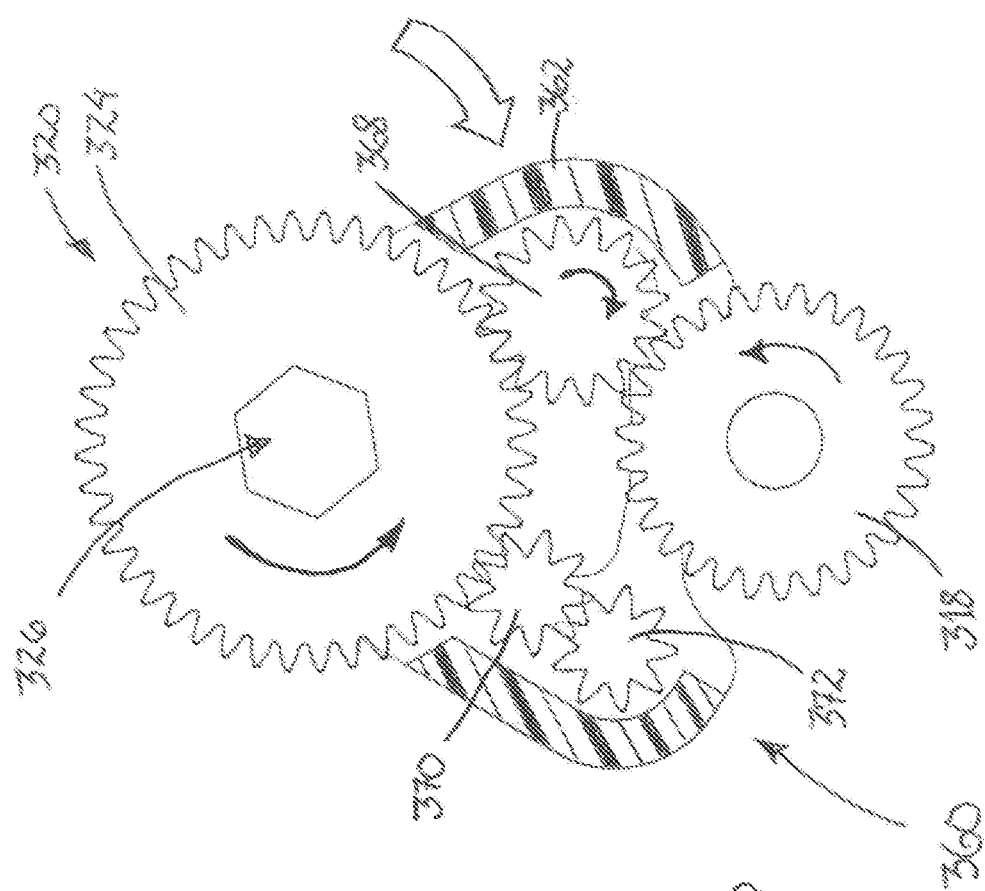
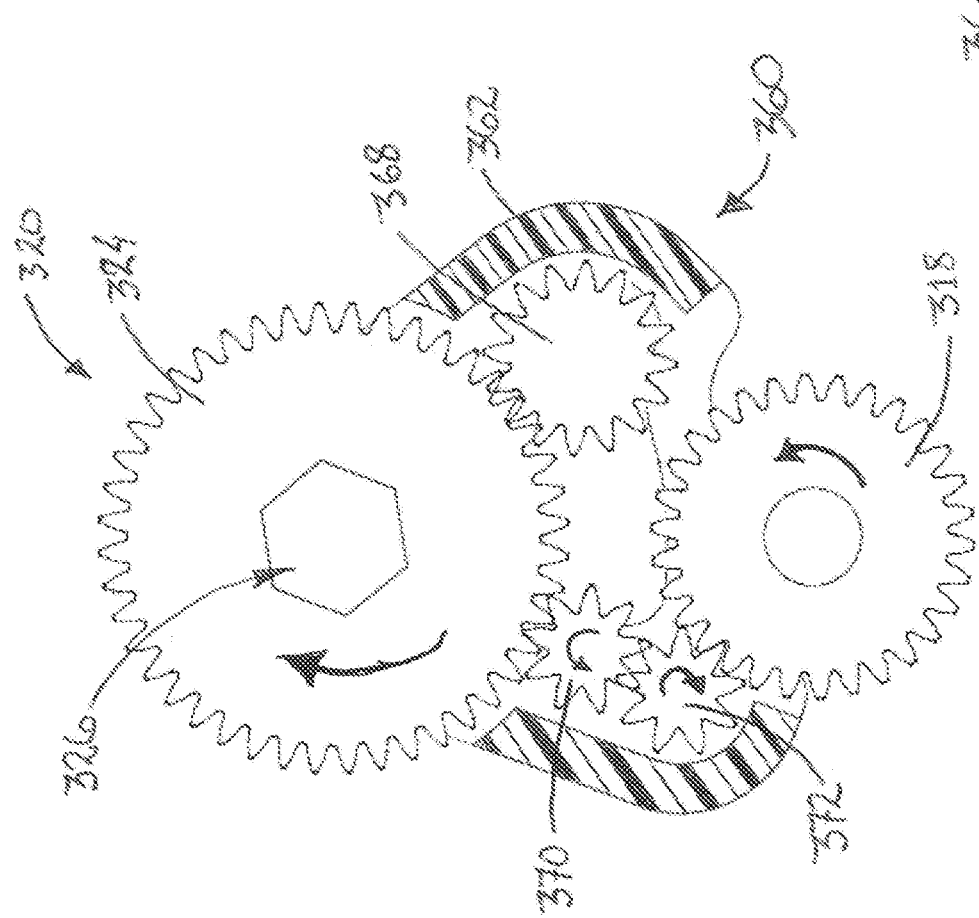
Fig. 18B
Fig. 18A

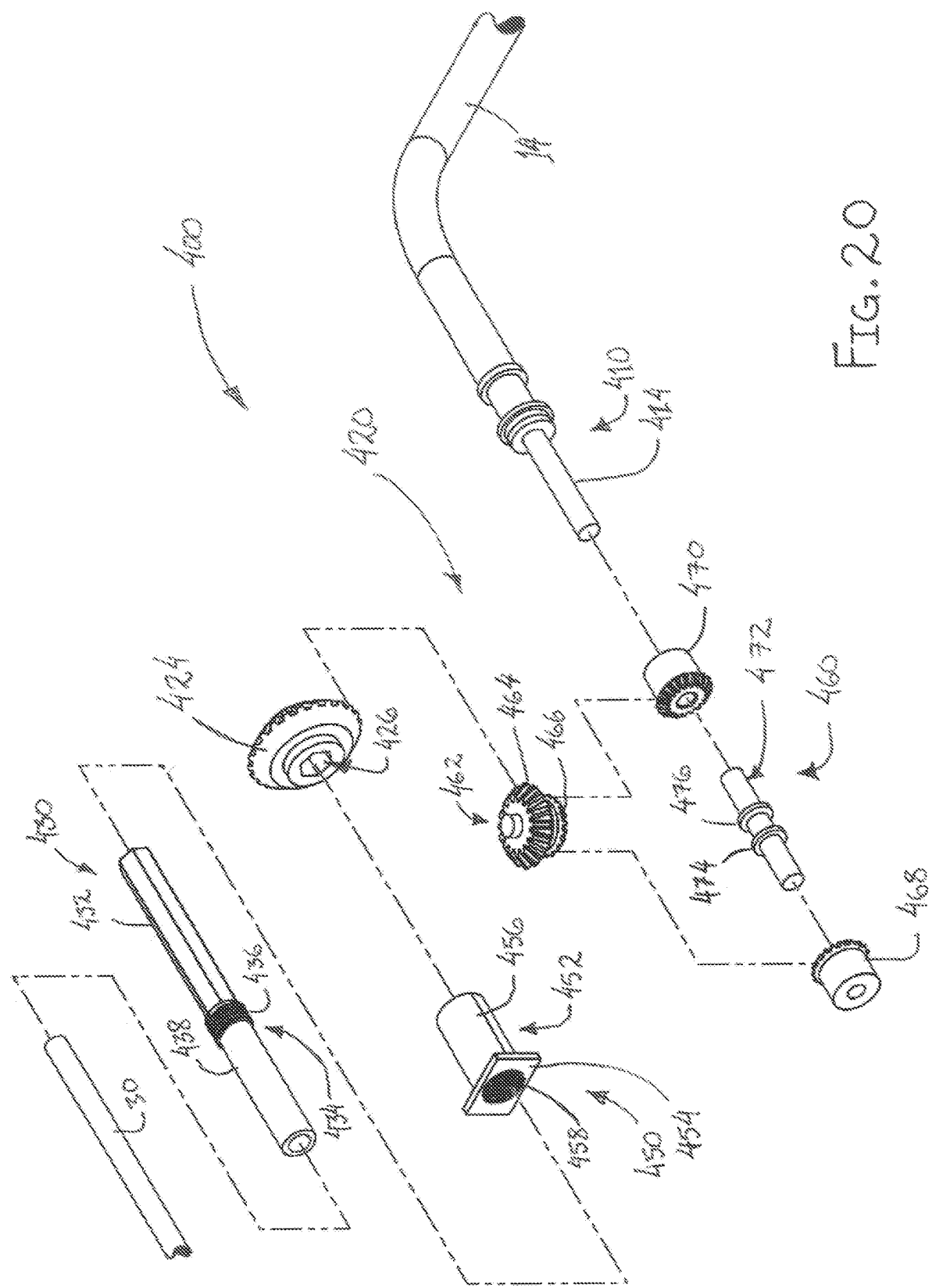

BIOPSY DEVICE WITH SELF-REVERSING CUTTER DRIVE

PRIORITY

This application claims priority to U.S. Provisional Patent App. No. 62/697,430 entitled "Biopsy Device with Self-Reversing Cutter Drive," filed on Jul. 13, 2018, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and. Collection of Soft Tissue," issued Jun. 18, 1996; U.S. Pat. No. 6,017,316, entitled "Vacuum Control System and Method for Automated. Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,432,065, entitled "Method for Using a Surgical Biopsy System with Remote Control for Selecting an Operational Mode," issued Aug. 13, 2002; U.S. Pat. No. 7,442,171, entitled "Remote Thumbwheel for a Surgical Biopsy Device," issued Oct. 8, 2008; U.S. Pat. No. 7,938, 786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No, 8,206,316, entitled "Tetherless Biopsy Device with Reusable Portion," issued Jun. 26, 2012; U.S. Pat. No. 8,241,226, entitled "Biopsy Device with Rotatable Tissue Sample Holder," issued Aug. 14, 2012; U.S. Pat. No. 8,702,623, entitled "Biopsy Device with Discrete Tissue Chambers," issued Apr. 22, 2014; U.S. Pat. No. 8,764,680, entitled "Handheld Biopsy Device with Needle Firing," issued Jul. 1, 2014; U.S. Pat. No. 8,938,285, entitled "Access Chamber and Markers for Biopsy Device," issued Jan. 20, 2015; U.S. Pat. No. 8,858,465, entitled "Biopsy Device with Motorized Needle Firing," issued Oct. 14, 2014; and U.S. Pat. No. 9,326,755, entitled "Biopsy Device Tissue Sample Holder with Bulk Chamber and Pathology Chamber," issued May 3, 2016. The disclosure of each of the above-cited U.S. Patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006, now abandoned; U.S. Pat. Pub. No. 2009/0131821, entitled "Graphical User interface For Biopsy System Control Module," published May 21, 2009, now abandoned; U.S. Pat. Pub. No. 2010/0152610, entitled "Hand Actuated Tetherless Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; and U.S. Pat. Pub. No. 2013/0324882, entitled "Control for Biopsy Device," published Dec. 5, 2013, now abandoned. The disclosure of each of the above-cited U.S. Patent Application Publications, U.S. Non-Provisional Patent Applications, and U.S. Provisional Patent Applications is incorporated by reference herein.

In U.S. Pat. No. 7,831,290, entitled "MRI Biopsy Device Localization Fixture," issued on Nov. 9, 2010, the disclosure of which is incorporated by reference herein, a localization mechanism, or fixture, is described that is used in conjunction with a breast coil for breast compression and for guiding a core biopsy device during prone biopsy procedures in both open and closed Magnetic Resonance Imaging (MRI) machines. The localization fixture includes a three-dimensional Cartesian positionable guide for supporting and orienting an MRI-compatible biopsy device, and, in particular, a cannula/sleeve to a biopsy site of suspicious tissues or lesions. Another merely illustrative localization mechanism used for guiding a core biopsy device is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy device. For instance, a combination of an obturator and targeting cannula/sleeve may be introduced through a breast to a biopsy site via the guide cube, with proper positioning confirmed using MRI imaging. The obturator may then be removed, and the needle of a biopsy device may then be inserted through the targeting cannula/sleeve to reach the targeted lesion.

In some MRI-guided biopsy procedures, the biopsy device can be powered by an elongate rotary drive cable. This configuration permits electrical components such as motors and electronics a distance from MRI equipment to minimize interference. However, in some circumstances, this configuration can create challenges due to the rotary drive cable exhibiting a phenomenon known as "cable whip." This phenomenon occurs when torque imbalances build in the rotary drive cable and cause the cable to physically move. This phenomenon can result in procedural delays. Accordingly, it may be desirable to include certain features within a biopsy device to decrease the occurrence of "cable whip."

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 7C depicts yet another perspective view of the cutter drive mechanism of FIG. 2, with the cutter drive mechanism in an advanced position;

FIG. 7D depicts still another perspective view of the cutter drive mechanism of FIG. 2, with the cutter drive mechanism returned to the intermediate position of FIG. 7B;

FIG. 15 depicts a perspective view of another exemplary alternative cutter drive mechanism for incorporation into the biopsy device of FIG. 1;

FIG. 18A depicts a front cross-sectional view of the gearbox assembly of FIG. 17, with the gearbox assembly in a second stage position;

FIG. 18B depicts another front cross-sectional view of the gearbox assembly of FIG. 17, with the gearbox assembly in a first stage position;

FIG. 20 depicts an exploded perspective view of the cutter drive mechanism of FIG. 19;

Figure 1:
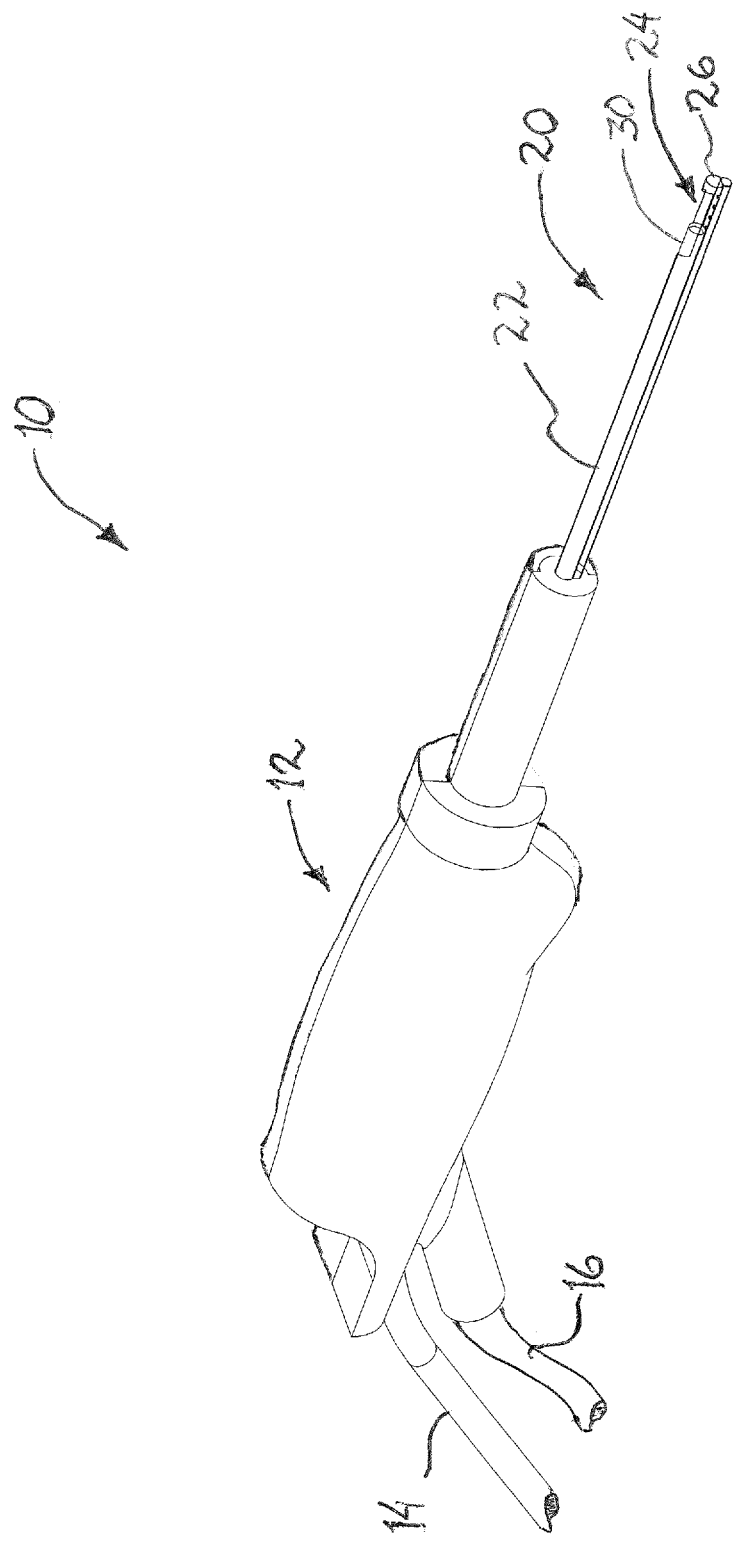
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects; embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Biopsy Device

FIG. 1 shows an exemplary biopsy device (10) that is generally configured for use in an MRI guided breast biopsy procedure. Biopsy device (10) includes a body (12) and a needle (20) extending distally therefrom. Body (12) is generally configured for gripping by a single hand of an operator. However, in some examples body (12) can also be configured for use with a biopsy fixture or manipulator device. Although not shown, it should be understood that in some examples, body (12) can be formed by one or more components. For instance, in some examples body (12) is formed by a combination of a probe and a holster. In such examples, the holster can be reusable, and the probe can be disposable, Accordingly, suitable holsters can include certain reusable components such as motors, pumps, and/or transmissions. Meanwhile, suitable probes can include certain disposable components such as valves, seals, drive gears and/or transmissions, Moreover, suitable probes can be configured to couple to needle (20) to permit disposability of both the probe and needle (20). Of course, the embodiments discussed above are merely examples and various configurations for body (12) may be used as will be understood by those of ordinary skill in the art in view of the teachings herein.

A plurality of cables (14, 16) extend proximally from body (12). In the present example, cables (14, 16) can be used to couple body (12) to one or more control modules (not shown) to provide communication of fluids and or control signals to body (12). For instance, in the present example cable (14) is configured as a rotary drive cable. In this configuration, cable (14) can be coupled to a motor disposed within a control module to provide rotary power to body (12). As will be described in greater detail below, body (12) encloses certain drive features that can be powered by cable (14). Thus, cable (14) is configured to remotely power biopsy device (10) via a control module. Alternatively, in some examples, cable (14) can be configured as an electrical or pneumatic cable. In such examples, an electric or pneumatic motor can be enclosed within body (10) to thereby power biopsy device (10) via a control module.

In some contexts, the configuration of cable (14) as a rotary drive cable can be particularly advantageous. For instance, in MRI guided biopsy procedures, sensitive equipment within an MRI suite can make it undesirable to include substantial amounts of metal within biopsy device (10). Thus, to reduce the presence of metals within biopsy device (10), motors and other related metallic drive components can be located within a control module that can be positioned outside of an MRI suite. Cable (14) can then communicate rotary power that would otherwise be provided by a motor within biopsy device (10) to biopsy device (TO) from the control module. Although the examples described below are discussed within this context, it should be understood that various components described herein can be readily used in other contexts (e.g., stereotactic biopsy, ultrasonic biopsy, and etc.) where one or more motors can be included within body (12) of biopsy device (10).

Cable (16) can also be coupled to a control module to provide control of various functions to biopsy device (10). For instance, in the present example cable (16) includes one or more tubes or lumens to fluids such as vacuum, saline, and/or atmospheric air to biopsy device (10). As will be understood, communication of fluids to and from biopsy device (10) may be useful to assist with collecting and transporting tissue samples during a biopsy procedure. In addition to communication of fluid, cable (16) can also include one or more electrical wires to communicate electrical signals between biopsy device (10) and the control module. For instance, in some examples biopsy device (10) can include various sensors and/or input features to monitor and/or manipulate various operational parameters of biopsy device (10). Thus, electrical wires in cable (16) can be used to communicate signals from such sensors and/or input features to the control module from biopsy device (10). Of course, the above description of cable (16) is merely an example. Accordingly, cable (16) can take on a variety of other configurations in other examples as will be apparent to those of ordinary skill in the art in view of the teachings herein.

As described above, various control modules can be used in connection with biopsy device (10) via cables (14, 16). A range of preprogrammed functionality may be incorporated into such control modules to assist in taking tissue samples. Suitable control modules are generally configured to control and power biopsy device (10) during a biopsy procedure, Examples of suitable programming for a given control module are disclosed in U.S. Pat. No. 6,752,768, entitled "Surgical Biopsy System with Remote Control for Selecting an Operational Mode," issued on Jun. 22, 2004, the disclosure of which is incorporated by reference herein.

As will be understood, needle (20) is generally configured to sever and collect a plurality of tissue samples from a patient with a single insertion. Needle (20) of the present example includes a hollow elongate cannula (22) and distal tip (26) disposed on the distal end of cannula (22). Although distal tip (26) of the present example is shown as having a generally blunt configuration, it should be understood that in other examples distal tip (26) can be configured as a sharp tip including one or more blades or sharpened surfaces. As will be described in greater detail below, such a sharp tip is generally unnecessary in the present example because needle (20) is generally configured for use with a targeting set that is used to penetrate the tissue of a patient prior to insertion of needle (20). However, it should be understood that in other examples needle (20) can be configured for penetration of a patient directly. Thus, needle (20) can be equipped with either a sharp tip or a blunt tip depending on the particular desired use of needle (20).

Proximally of distal tip (26), cannula (22) defines a lateral aperture (24). Lateral aperture (24) is generally in communication with the hollow interior of cannula (22) such that lateral aperture (24) is configured to receive prolapsed tissue therethrough. As will be described in greater detail below, a cutter (30) can be used in connection with lateral aperture (24) to sever tissue samples once tissue is prolapsed through lateral aperture (24).

Cutter (30) is slidably disposed within the hollow interior of cannula (22). Cutter (30) defines a cutter lumen extending from the distal end of cutter to the proximal end. As will be described in greater detail below, cutter (30) is configured to be rotated and translated relative to lateral aperture (24) by various drive components within body (12). This rotation and translation of cutter (30) is generally configured to sever tissue samples when tissue is prolapsed through lateral aperture (24). To promote the severing of tissue samples via cutter (30), at least a portion of the distal end of cutter (30) can be sharpened.

To accommodate cutter (30), cannula (22) can include a cutter lumen extending longitudinally through cannula (22). Although not shown, it should be understood that in some examples cannula (22) can also include an additional lumen oriented laterally relative to the cutter lumen. In such examples, this lateral lumen is configured to communicate fluid directly to lateral aperture (24). For instance, in some examples vacuum can be communicated to lateral aperture (24) via the lateral lumen to provide additional suction to prolapse tissue through lateral aperture (24). In addition, or in the alternative, in some examples atmospheric air can be supplied via the lateral lumen. In such examples, atmospheric air can be beneficial to provide a pressure differential between the proximal and distal ends of a tissue sample being transported through cutter (30). In some examples a suitable lateral lumen can be in the form of a separate discrete lumen adjacent to the cutter lumen. In other examples, a suitable lateral lumen can simply be defined by the space between cannula (22) and cutter (30). Still other configuration of a suitable lateral lumen will be apparent to those of ordinary skill in the art in view of the teachings herein.

Although not shown, it should be understood that in some contexts needle (20) can be used in connection with a targeting assembly and/or other device(s) to assist with localizing needle (20) within a patient. For instance, during an MRI guided biopsy procedure a targeting set including an obturator disposed within a targeting cannula can be used to initially localize a suspicious lesion within a patient. Suitable targeting sets are generally comprised of MRI compatible materials so that they can be used in the presence of high electromagnetic fields generated by Mill coils. Accordingly, it should be understood that the combination of the obturator and the targeting cannula can be first placed within a patient under MRI guidance. Once placed as desired, the obturator can be removed from the targeting cannula, while the targeting cannula remains in place within the patient. Needle (20) can then be introduced into the patient through the targeting cannula for the collection of tissue samples. One or more examples of suitable targeting sets and associated localization devices are described in U.S. Pat. No. 8,932,233, entitled "MRI Biopsy Device," issued on Jan. 13, 2015, the disclosure of which is incorporated by reference herein.

Although not shown, it should be understood that in some examples biopsy device (10) can be equipped with a tissue sample holder or other sample management device. As described above, tissue samples can be severed via cutter (30) and then transported through cutter (30) to a proximal portion of biopsy device (10). In some examples, the proximal end of cutter (30) is in communication with a tissue sample holder to collect the severed tissue sample. A suitable tissue sample holder can take a variety of forms. For instance, in some examples a suitable tissue sample holder can simply be a surface upon which tissue samples can be deposited and later collected by an operator. In other examples, a suitable tissue sample holder can include one or more trays for collection of tissue samples. In such tissue sample holders, a suitable tray can be configured as a single basket to hold tissue samples in bulk. Alternatively, such tissue sample holders can include multiple trays configured to hold one or more tissue samples. Where multiple trays are used, the tissue sample holder can be configured to move the trays relative to the cutter to selectively control which tray tissue samples are deposited into. Examples of suitable tissue sample holders are described in U.S. Pat. No. 8,932,233, entitled "MRI Biopsy Device," issued on Jan. 13, 2015; US Pat. Pub. No. 2012/0065542, entitled "Biopsy Device Tissue Sample Holder with Removable Tray," published on Mar. 15, 2012; and U.S. Pat. No. 8,968,212, entitled "Biopsy Device with Motorized Needle Cocking," issued on Mar. 3, 2015, the disclosures of which are incorporated by reference herein.

II. Exemplary Cutter Drive Mechanism

As described above, various internal components of biopsy device (10) can be powered with a rotary drive cable such as cable (14). As also described above, this configuration can be particularly desirable in the context of MRI guided procedures because use of a rotary drive cable permits elements of a biopsy system that might otherwise interfere with sensitive MRI equipment (e.g., motors) to be segregated from the most sensitive MRI equipment. However, where rotary drive cables are used, it may be desirable to reduce or eliminate changes in torque within such rotary drive cables. For instance, when a rotary drive cable reverses rotation direction, the corresponding change in torque can cause the rotary drive cable to deform creating kinks. Moreover, deformations can be sudden under certain circumstances, causing the rotary drive cable to "whip" or rapidly and unpredictably move about within a given space. Thus, it is generally desirable to reduce the need to change the rotation direction of a rotary drive cable during a biopsy procedure.

Various examples of mechanisms that can be readily incorporated into biopsy device (10) to reduce the need to change the rotation direction of a rotary drive cable are described below. Although several different mechanisms are described herein, it should be understood that various alternative mechanisms will be apparent to those of ordinary skill in the art in view of the teachings herein.

FIGS. 2-6 show an exemplary cutter drive mechanism (100) that can be readily incorporated into body (12) of biopsy device (10) to drive rotation and translation of cutter (30). Cutter drive mechanism (100) is generally configured to simultaneously rotate and translate cutter (30) through a predetermined movement pattern with a rotary input from cable (14) in a single rotation direction. As will be described in greater detail below, the predetermined movement pattern of cutter (30) generally involves cutter (30) rotating continuously in a single direction while cutter (30) also translates first distally and then proximally. Accordingly, it should be understood that as a consequence of this configuration, it is not necessary to reverse the rotary input of cable (14) to translation cutter (30) from distal translation to proximal translation.

Figure 2:
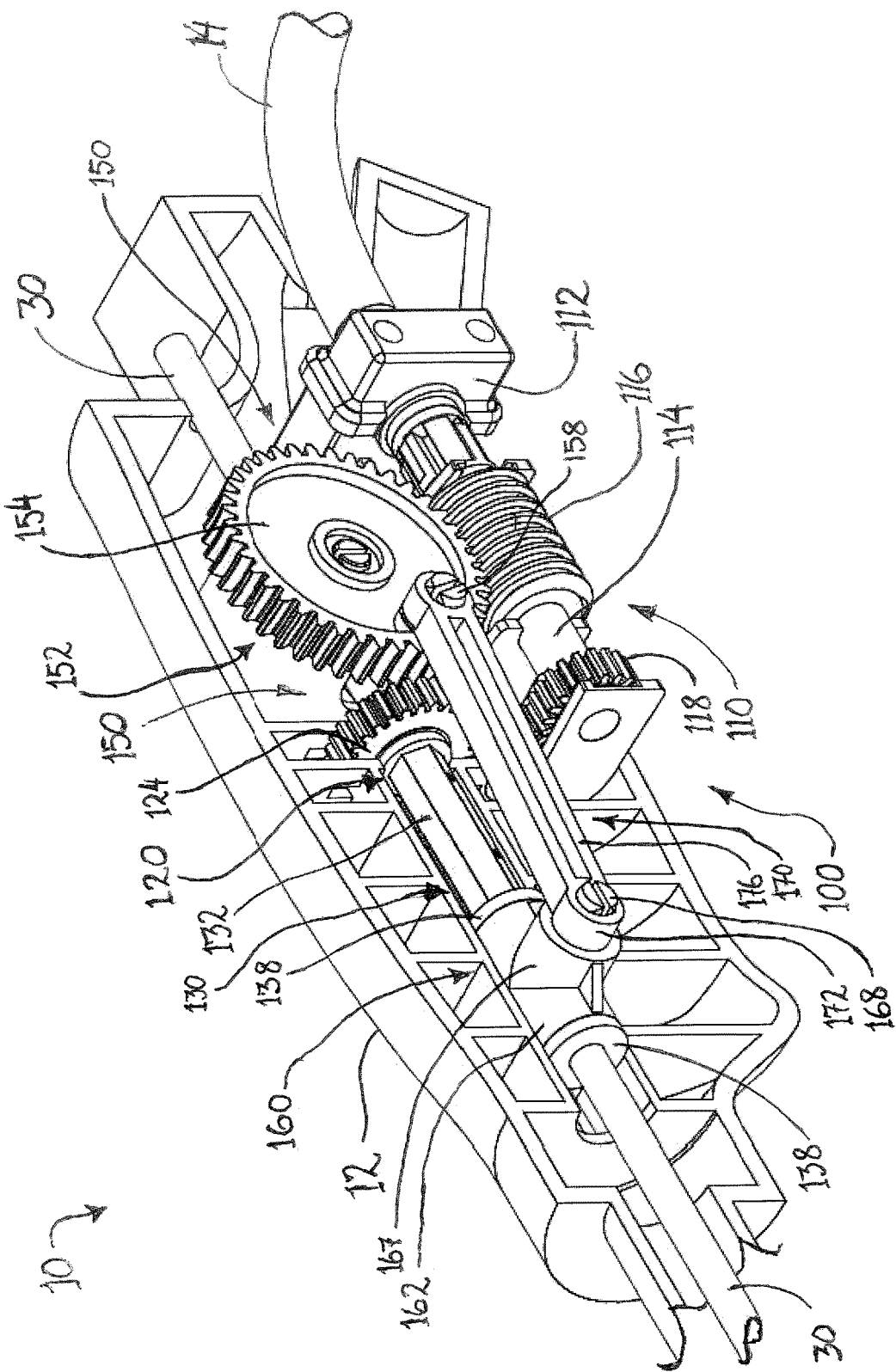
FIG. 2 depicts a perspective view of a cutter drive mechanism of the exemplary biopsy device of FIG. 1.

Cutter drive mechanism (100) comprises an input assembly (110), a rotation assembly (120), and a translation assembly (150). As best seen in FIG. 2, input assembly (110) is generally configured to couple to cable (14) to provide mechanical power to both rotation assembly (120) and translation assembly (150). Input assembly (110) includes a rotatory coupler (112) that is configured to permit cable (14) to selectively couple to input assembly (110). Although not shown, it should be understood that rotary coupler (112) can include a variety of features to support selective coupling of cable (14). By way of example only, suitable features may include gears, bearings, fasteners, and/or etc.

It should be understood that in the present example cable (14) is not permanently attached to input assembly (110). Instead, cable (14) can be selectively decoupled from input assembly (110) when biopsy device (10) is not in use. In some circumstances this feature is desirable to promote flexibility, ease of use, and ease of storage of biopsy device (10). Thus, it should be understood that this feature is merely optional and that in some examples cable (14) is permanently coupled to indexing assembly (110).

Input assembly (110) further includes a shaft (114) extending distally from rotary coupler (112). Shaft (114) is generally configured to transfer rotary motion of cable (14) to various components of input assembly (110) as will be described in greater detail below. Shaft (114) includes a translation actuator (116) and a rotation actuator (118). In the present example, actuators (116, 118) are of integral construction with shaft (114). However, it should be understood that in other examples actuators (116, 118) can be separate from shaft (114) and attached thereto by various fastening techniques such as adhesive bonding, mechanical fastening, and/or etc.

Translation actuator (116) is disposed proximally relative to rotation actuator (118) and is generally configured to engage various components of translation assembly (150). In the present example, translation actuator (116) is shown as a worm gear. However, as will be described in greater detail below, it should be understood that various alternative actuators can be used as will be appreciated by those of ordinary skill in the art.

Rotation actuator (118) is positioned distally relative to translation actuator (116) at the distal end of shaft (114). Rotation actuator (118) is generally configured to engage various components of rotation assembly (120) as will be described in greater detail below. In the present example, rotation actuator (118) is shown as a spur gear. However, as will be described in greater detail below, it should be understood that various alternative actuators can be used as will be appreciated by those of ordinary skill in the art.

Figure 3:
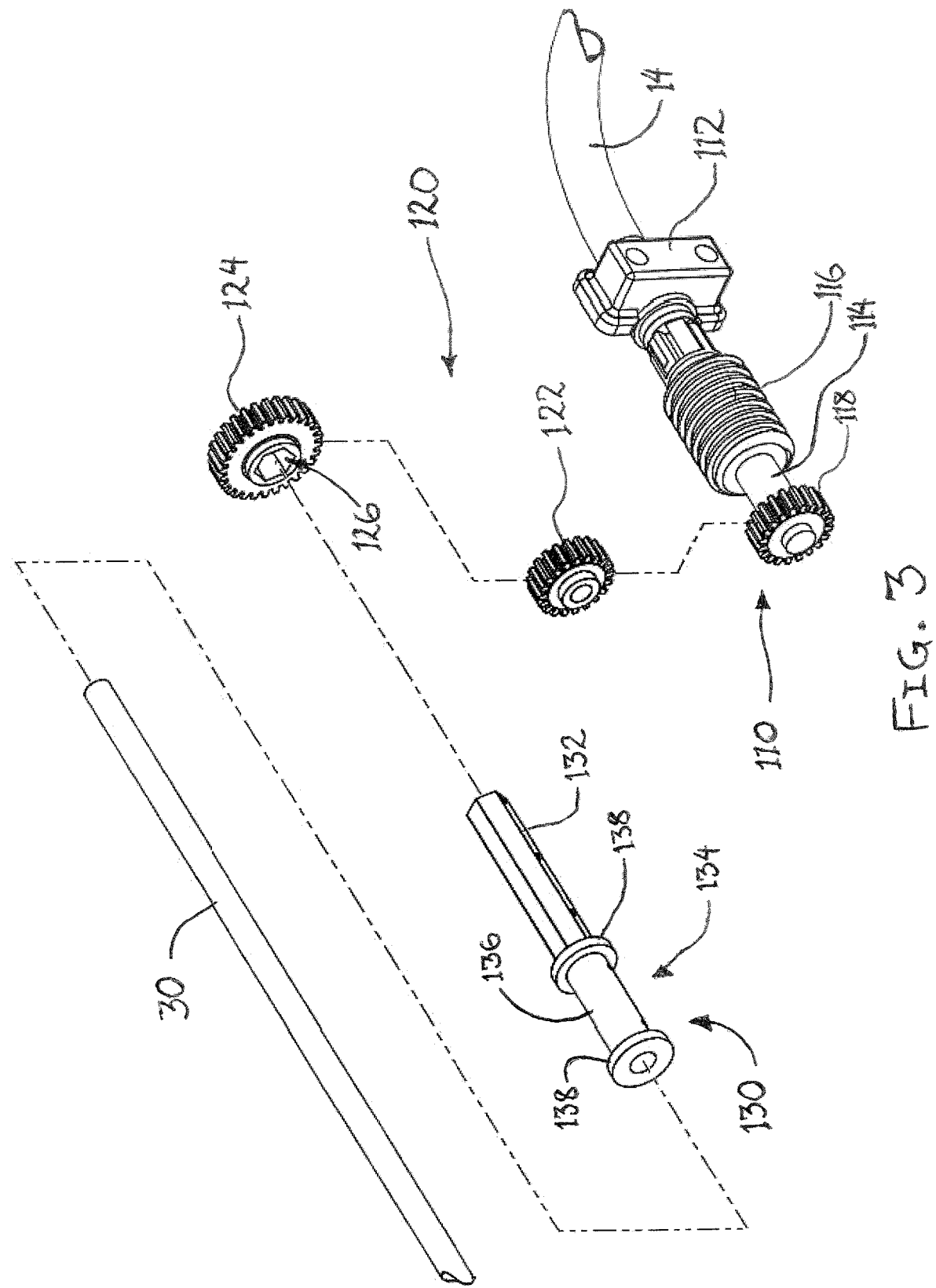
FIG. 3 depicts an exploded perspective view of a rotation assembly of the cutter drive mechanism of FIG. 2.

Rotation assembly (120) is best seen in FIG. 3, As can be seen, rotation assembly (120) comprises an intermediate actuator (122), a keyed actuator (124), and a cutter driver (130). Intermediate actuator (122) is generally configured to engage both keyed actuator (124) and rotation actuator (118) of input assembly (110). In the present example, intermediate actuator (122) is shown as a spur gear. Thus, the spur gear of intermediate actuator (122) is configured to mesh with the spur gear of rotation actuator (118) to transfer rotation of shaft (114) to keyed actuator (124). Although intermediate actuator (122) is shown as a spur gear in the present example, it should be understood that in other examples intermediate actuator (122) can take on a variety of forms such as a belt drive, a chain drive, and/or etc. Additionally, although the present example is shown as included only a single intermediate actuator (122), it should be understood that in other examples a plurality of intermediate actuators (122) can be used. Alternatively, in still other examples, intermediate actuator (122) can be eliminated entirely and keyed actuator (124) can engage directly with rotation actuator (118).

Keyed actuator (124) is generally configured to provide rotation from shaft (114) to cutter driver (130) to ultimately rotate cutter (30). In the present example, keyed actuator (124) is shown as a spur gear. Thus, the spur gear of keyed actuator (124) is configured to mesh with the spur gear of intermediate actuator (122). As described above, the spur gear of intermediate actuator (122) in turn is configured to mesh with the spur gear of rotation actuator (118) to transfer rotation of shaft (114) to keyed actuator (124), which ultimately results in rotation of cutter (30) by cutter driver (130).

Keyed actuator (124) additionally defines a bore (126) extending therethrough. Bore (126) is generally sized to accommodate the combination of cutter driver (130) and cutter (30) such that keyed actuator (1 4) is generally coaxial with cutter (30). Bore (126) is further configured to transfer rotation of keyed actuator (124) to cutter driver (30), while also permitting at least some translation of cutter driver (30) relative to keyed actuator (124). To transfer rotation of keyed actuator (124) to cutter driver (130) while still allowing translation of cutter driver (130) relative to keyed actuator (124), keyed actuator (124) is generally "keyed" to rotatably engage cutter driver (130).

Although the term "keyed" may be understood by some to convey a particular structure, it should be understood that no such limitation is intended. For instance, in the present example bore (126) defines a generally hexagonal cross-sectional shape to make keyed actuator (124) "keyed," However, it should be understood that in other examples a variety of alternative shapes and configurations can be used. For instance, in some examples bore (126) can define a square, triangular, oval-shaped, octagonal, or other suitable cross-sectional shapes. Alternatively, in other examples bore (126) can be cylindrical in shape with an additional square or rectangular key included within keyed actuator (124) to correspond to a mating channel included within cutter driver (130). Of course, various other "keyed" configurations can be used as will be apparent to those of ordinary skill in the art in view of the teachings herein.

Figure 4:
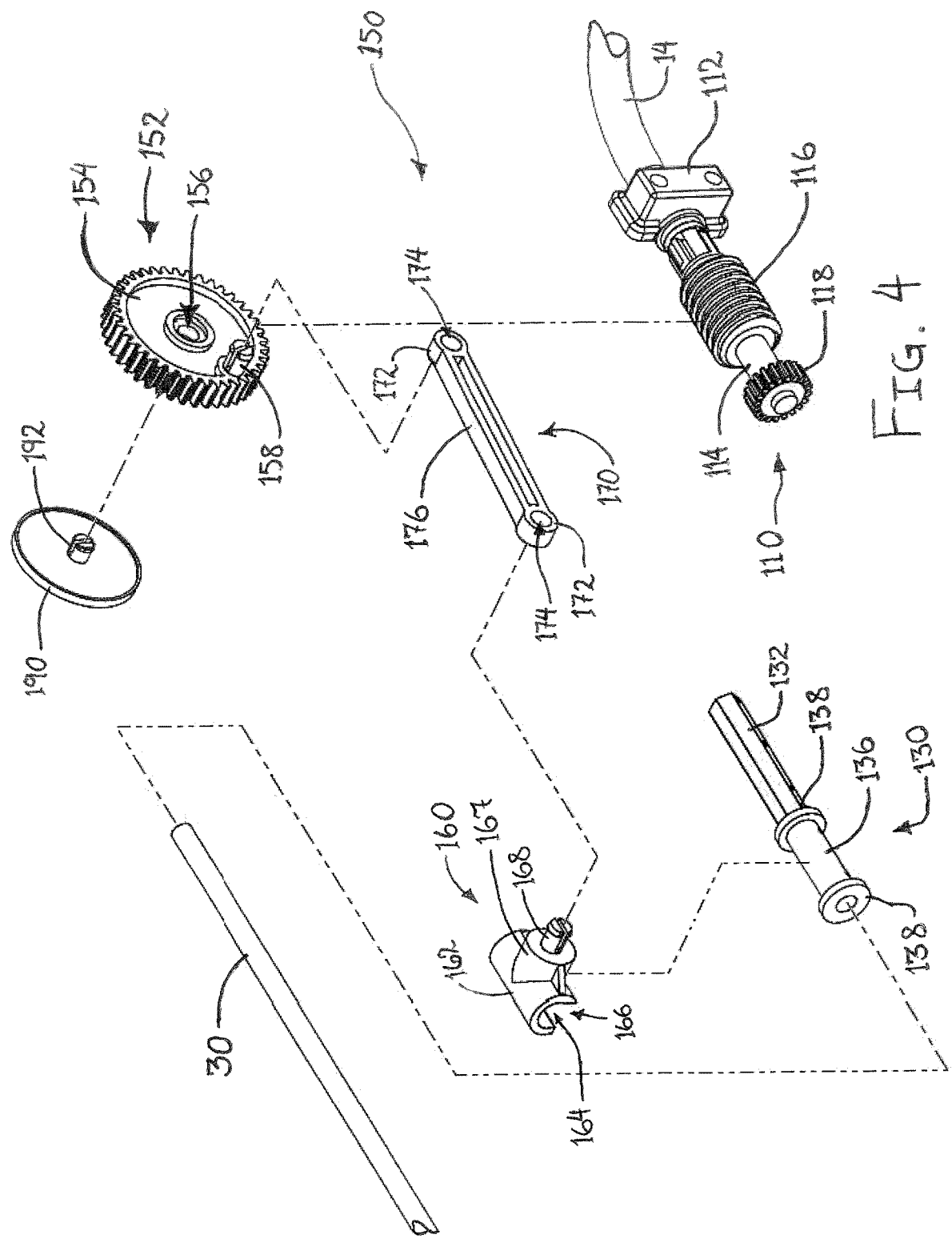
FIG. 4 depicts an exploded perspective view of a translation assembly of the cutter drive mechanism of FIG. 2.

Cutter driver (130) is shown in both FIGS. 3 and 4. As will be described in greater detail below, cutter driver (130) engages with both rotation assembly (120) and translation assembly (150) to manipulate cutter (30) during a biopsy procedure. Cutter driver (130) is generally overmolded or otherwise fixedly secured to cutter (30). To engage rotation assembly (120), cutter driver (130) includes a rotation portion (132). Rotation portion (132) defines a generally hexagonal cross-sectional shape that corresponds to the hexagonal shape of bore (126) in keyed actuator (124). Rotation portion (132) generally extends for a length that corresponds to the range of translation of cutter (30). In some examples, this range of motion generally corresponds to the length of lateral aperture (24), although other suitable ranges of motion can be used.

As will be described in greater detail below, cutter driver (130) is also configured to engage at least a portion of translation assembly (150). To permit this engagement, cutter driver (130) includes translation portion (134) disposed distally of rotation portion (132). Translation portion (134) includes a cylindrical receiver (136) disposed between two stops (138). Cylindrical receiver (136) defines a generally cylindrical shape that is configured to receive a portion of translation assembly (150) as will be described in greater detail below. Each stop (138) in the present example is configured as a flange extending outwardly from cylindrical receiver (136) on each side of cylindrical receiver (136). As will be described in greater detail below, the combination of both stops (138) is generally configured to permit at least a portion of translation assembly (150) to translate cutter (30) via cutter driver (130).

FIG. 4 shows translation assembly (150) in greater detail. As can be seen, translation assembly (150) includes a translator (152), a coupler (160), and a connector (170). Translator (152) of the present example is configured as a worm wheel with a diameter that generally corresponds to the length of lateral aperture (24) or the entire translation distance of cutter (30). As will be described in greater detail below, translator (152) is generally configured to translate cutter (30) in response to rotation of translation actuator (116) via various component of translation assembly (150). In the present configuration as a worm wheel, translator (152) meshes with the worm gear of translation actuator (116) of input assembly (110). Thus, translator (152) rotates about an axis oriented perpendicularly to the rotation axis of translation actuator (116). As will be described in greater detail below, this permits translator (152) to rotate in line with the translation axis of cutter (30) and thereby permit translator (152) to translate cutter (30).

Translator (152) includes a body (154) defining a plurality of teeth, a rotation bore (156), and a translation post (158) extending from a single side of body (154). Although not shown, it should be understood that body (154) is received within a portion of body (12) of biopsy device (10). For instance, in some examples body (12) of biopsy device (10) includes a cylindrical bore configured for receipt of translator (152). This configuration permits translator (152) to rotate, while remaining in a fixed position relative to the rotation axis of translator (152). To support rotation of translator (152), rotation bore (156) is configured to receive a rotation post (192) defined by a bushing (180). Hub (190) can be likewise received within body (12) of biopsy device (10), but by compression fitting or adhesive bonding to provide a fixed point of rotation for translator (152). To provide ease of assembly, rotation post (192) of hub (190) is configured as a snap fit assembly. In the present example, rotation post (192) includes two resilient arms with an outwardly oriented tooth on each arm. However, it should be understood that in other examples, numerous alternative couplings can be used including alternative snap fit assemblies and/or mechanical fasteners.

Translation post (158) of translator (152) extends laterally from body (154) of translator (152). Translation post (158) is positioned adjacent to the outer diameter of body (154). Thus, for every rotation of body (154) via teeth, translation post (158) is configured to move through a circular movement pattern generally corresponding to the diameter of body (154). As will be described in greater detail below, this positioning of translation post (158) is generally configured to convert rotation of translator (152) into translation motion for other portions of translation assembly (150).

To promote ease of assembly, translation post (158) of the present example s generally configured as a snap fit coupling. By way of example only, a suitable snap fit coupling can include two resilient arms with each arm having an outwardly oriented tooth. In other examples, translation post (158) can include a variety of alternative coupling features. Suitable coupling features can be snap fit in configuration or can alternatively be configured as mechanical fasteners.

Figure 6:
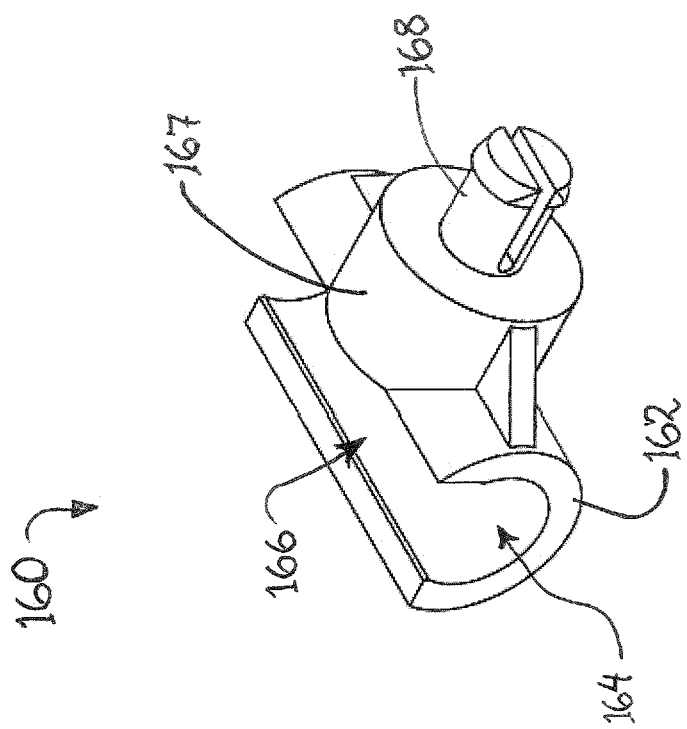
FIG. 6 depicts a perspective view of a coupler of the translation assembly of FIG. 4.
Figure 5:
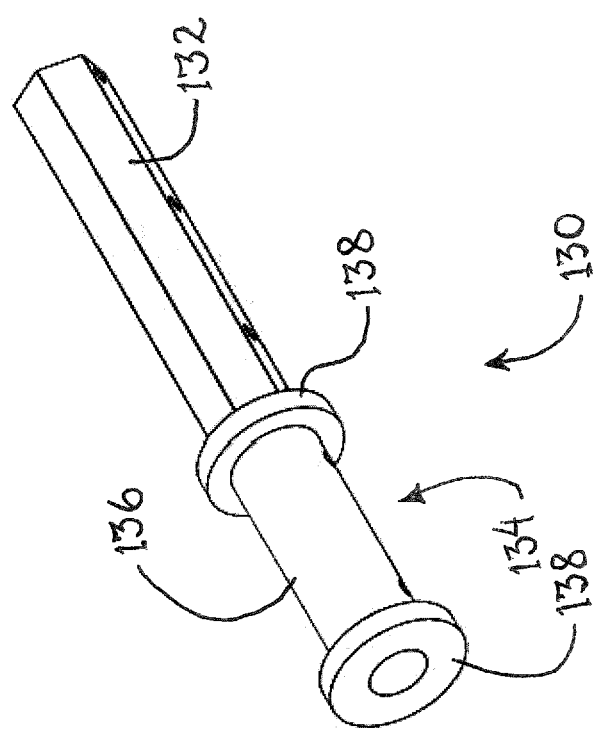
FIG. 5 depicts a perspective view of a cutter driver of the cutter drive mechanism of FIG. 2.

Coupler (160) is best seen in FIG. 6. As can be seen, coupler (160) includes a semi-cylindrical body (162), and a translation post (168) extending outwardly from semi-cylindrical body (162). As will be understood, coupler (160) is generally configured to fasten to a portion of cutter driver (130) to translate cutter (30) through cutter driver (130) when coupler (160) is acted upon by translator (152) via connector (170). To permit fastening of coupler (160) to cutter driver (130), semi-cylindrical body (162) defines a semi-cylindrical bore (164) generally corresponding to the outer diameter of cylindrical receiver (136) of cutter driver (130). Semi-cylindrical body (162) further defines an open portion (166) adjacent to, and in communication with, semi-cylindrical bore (164). As can be seen, the combination of semi-cylindrical bore (164) and open portion (166) makes semi-cylindrical body (162) just greater than half-cylindrical in shape. This additional cylindrical extension of semi-cylindrical body (162), permits the portion of semi-cylindrical body (162) adjacent to open portion (166) to grip cutter driver (130), thereby providing a snap fit configuration.

Translation post (168) of coupler (160) extends laterally from semi-cylindrical body (162). In the present example, a spacer (167) is included between semi-cylindrical body (162) and translation post (168). Spacer (167) is generally configured to provide at least some additional setoff distance between translation post (168) and semi-cylindrical body (162) for alignment purposes. Thus, it should be understood that in some examples spacer (167) can have various lengths lengths depending on the positioning of various components as will be understood in view of the teachings herein.

To promote ease of assembly, translation post (168) of the present example is generally configured as a snap fit coupling. By way of example only, a suitable snap fit coupling can include two resilient arms with each arm having an outwardly oriented tooth. In other examples, translation post (168) can include a variety of alternative coupling features. Suitable coupling features can be snap fit in configuration or can alternatively be configured as mechanical fasteners.

Connector (170) is generally configured to mechanically couple translator (152) to coupler (160) to permit translator (152) to manipulate coupler (160). As can be seen in FIG. 4, connector (170) includes a linkage (176) extending between two receivers (172). Although linkage (176) is shown as a I-shaped rod in the present example, it should be understood that in other examples linkage (176) can take on a variety of forms. For instance, in some examples linkage (176) can be configured as a cylindrical rod, a square rod, a rectangular rod, a L-shaped rod, a C-shaped rod, or etc.

Receivers (172) are positioned on each end of linkage (176). Each receiver (172) includes a bore (174) that is sized to receive translation post (158, 168) of translator (152) or coupler (160), respectively. When a particular translation post (158, 168) is received within a particular bore (174) of receiver (172), each translation post (158, 168) is generally free to rotate within a given receiver (172) while remaining fixed relative to the axis of rotation. As will be described in greater detail below, this configuration generally permits connector (170) to pivot while transferring motion between translator (152) and coupler (160).

Figure 7A:
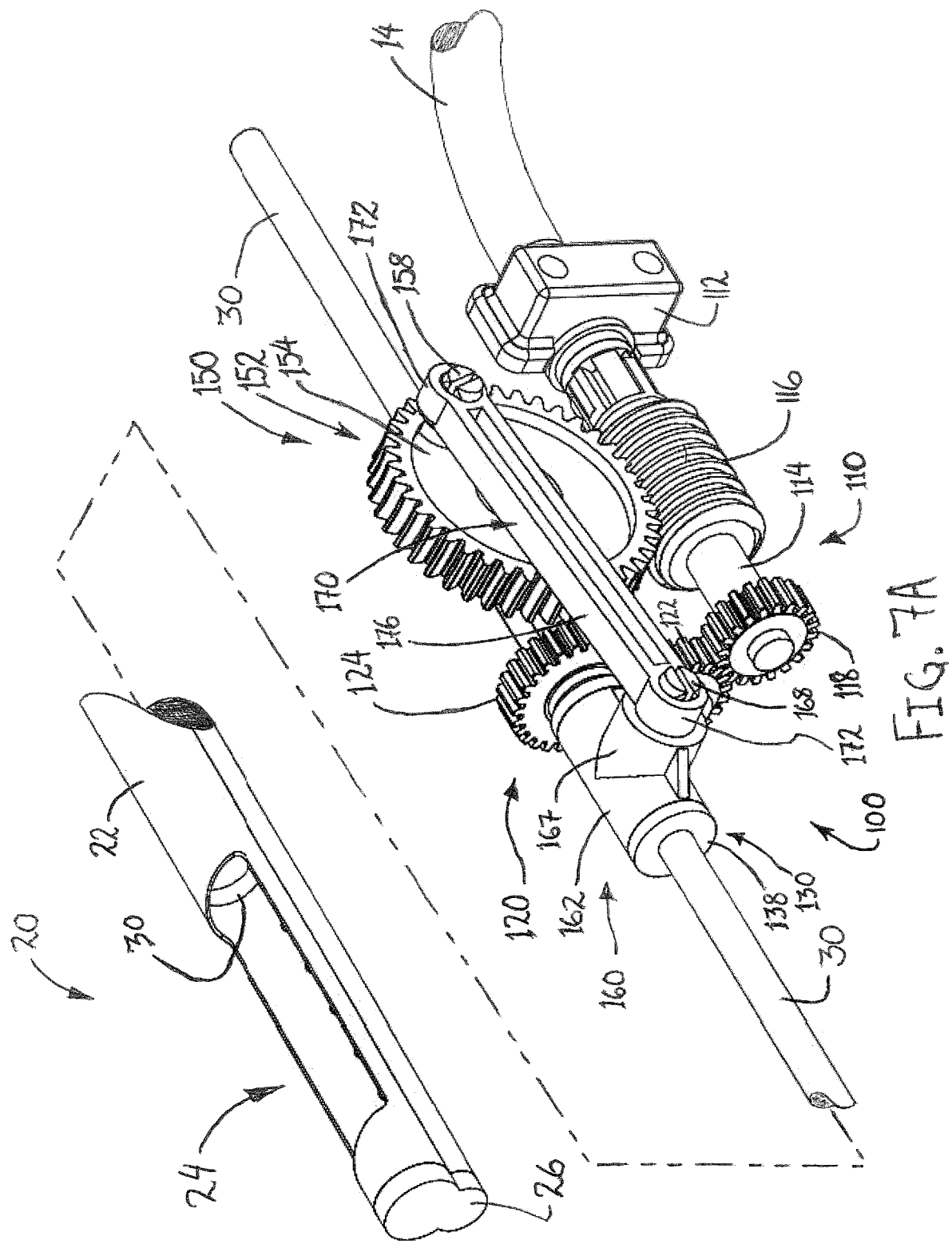
FIG. 7A depicts a perspective view of the cutter drive mechanism of FIG. 2, with the cutter drive mechanism in a retracted position.

FIGS. 7A through 7D show an exemplary use of cutter drive mechanism (100) to rotate and translate cutter (30). As seen in FIG. 7A, cutter drive mechanism (100) begins in an initial position. In the initial position, cutter (30) is retracted relative to the proximal end of lateral aperture (24). To achieve this position, actuator (116) is rotated so that translator (152) of translation assembly (150) is positioned with translation post (158) positioned in a proximal-most position. This in turn pulls cutter driver (130) proximally via coupler (160) and connector (170), which results in cutter (30) being pulled proximally to the proximal position shown in FIG. 7A.

Figure 7B:
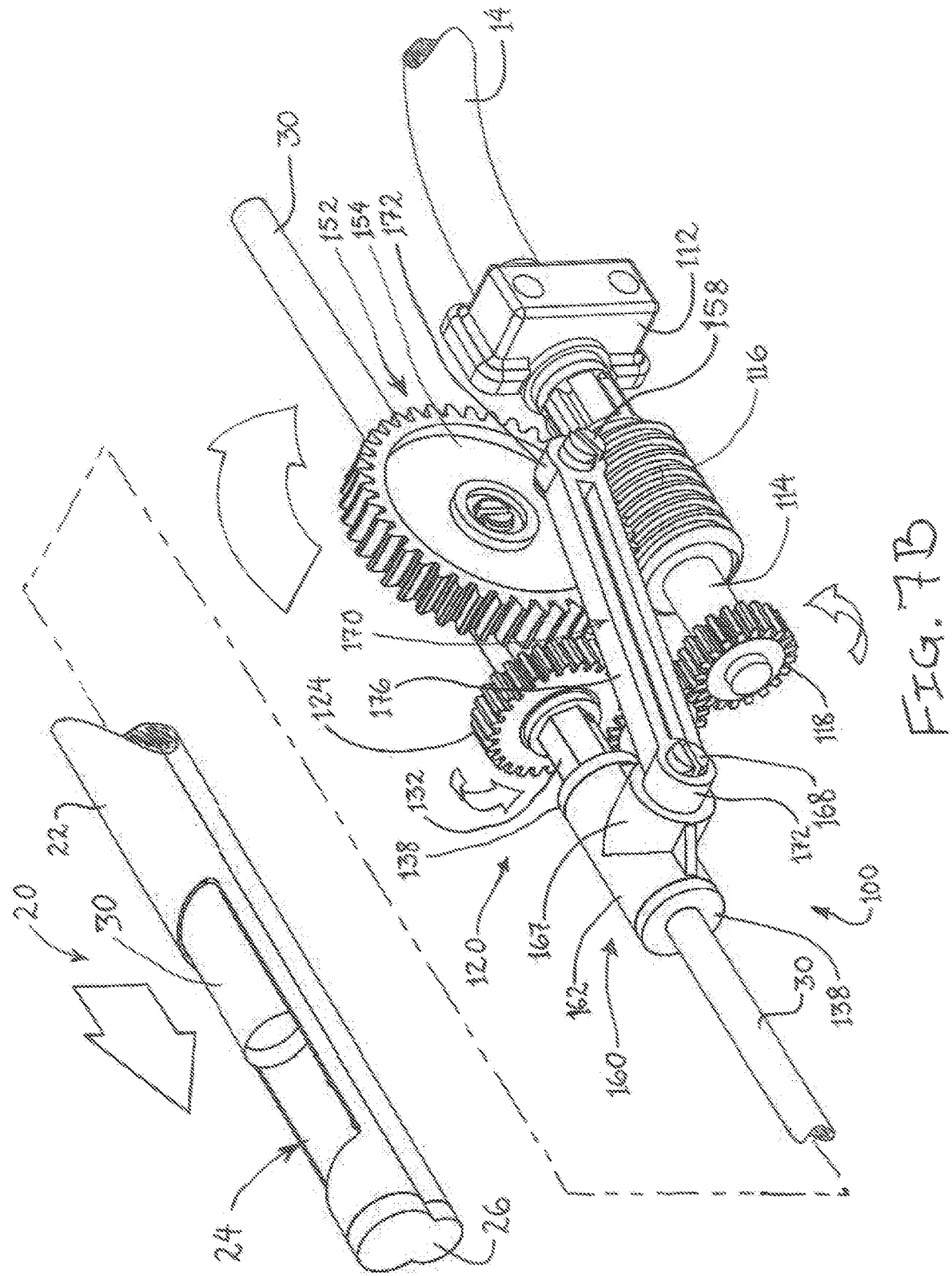
FIG. 7B depicts another perspective view of the cutter drive mechanism of FIG. 2, with the cutter drive mechanism in an intermediate position.
Figure 8:
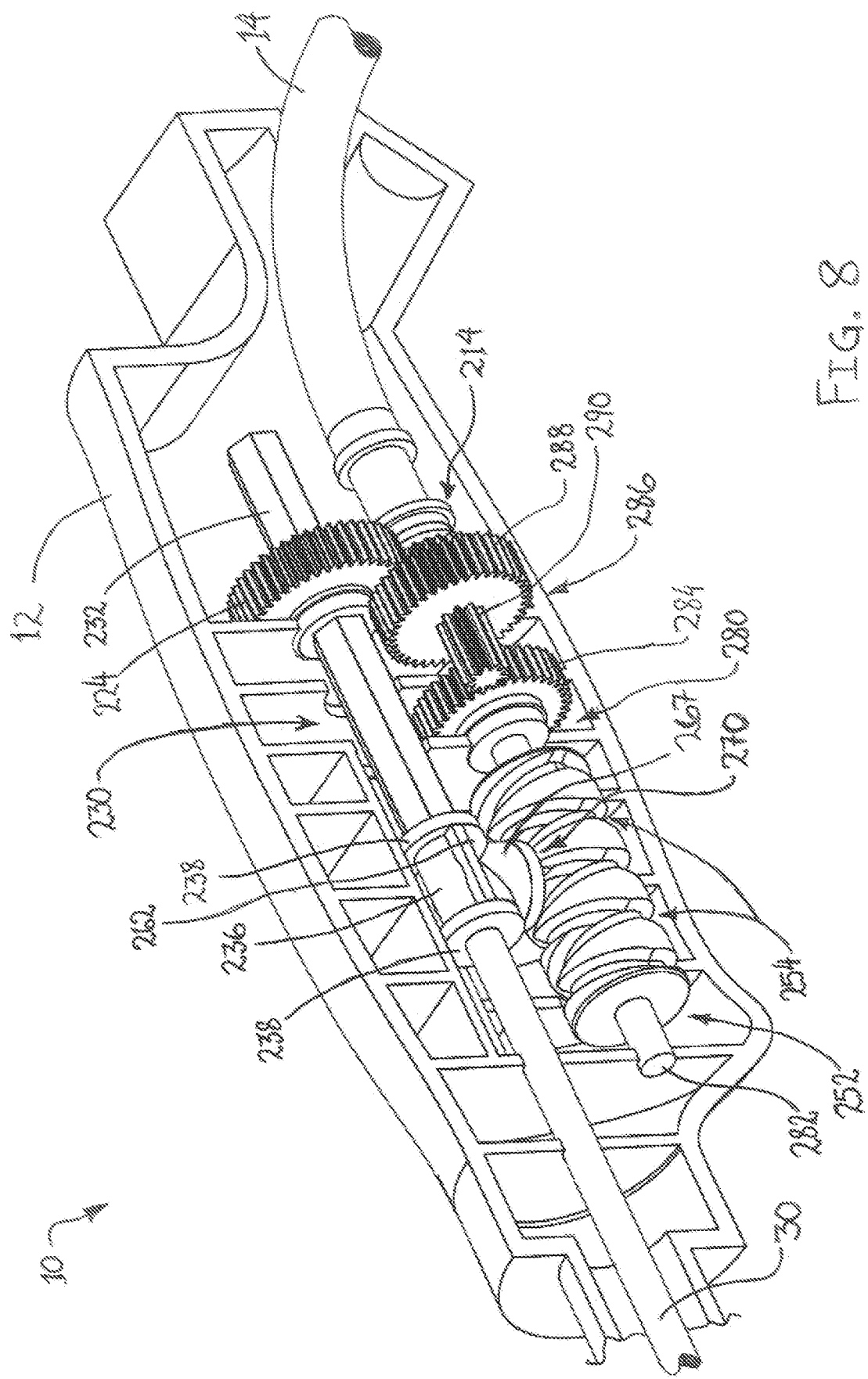
FIG. 8 depicts a perspective view of an exemplary alternative cutter drive mechanism for incorporation into the biopsy device of FIG. 1.

To advance cutter (30) distally, as shown in FIG. 7B, input assembly (110) rotates in so that actuator (118) rotates in a counterclockwise direction (relative to the visible face in FIG. 7B). Rotation of actuator (118) in the counterclockwise direction causes intermediate actuator (122) to rotate in a clockwise direction, which causes keyed. actuator (124) to rotate in a counterclockwise direction. Cutter (30) then rotates in a counterclockwise direction due to the keyed relationship between keyed actuator (124) and rotation portion (132) of cutter driver (130) and keyed actuator (124).

Simultaneously to rotation of cutter (30) via actuator (118), intermediate actuator (122), and keyed actuator (124), cutter (30) is also advanced via translator (152) of translation assembly (150). In particular, actuator (116) likewise rotates in a counterclockwise direction. Counterclockwise rotation of actuator (116) results in clockwise rotation of translator (152) (relative to the visible face in FIG. 7B). Clockwise rotation of translator (152) causes translation post (158) to be displaced transversely and longitudinally. The longitudinal displacement of translation post (158) pushes coupler (160) distally via connector (170). Connector (170) thereby acts on cutter driver (130) to translate cutter (30) distally. This movement then proceeds through the position shown in FIG. 7B until the distal end of cutter (30) is positioned distally of lateral aperture (24) as shown in FIG. 7C.

As discussed above, translation post (158) of translator (152) is displaced transversely and longitudinally while translating cutter (30) via connector (170) and coupler (160). Because of this, it should be understood that translation of cutter (30) is generally non-linear in axial translation speed. For instance, since translator (152) is circular in shape, translation post (158) will move relatively quickly in the longitudinal or axial direction when translation post (158) is positioned near the top and bottom portions of translator (152). Conversely, translation post (158) will move relatively slowly in the longitudinal or axial direction when translation post (158) is positioned near the tip and bottom portions of translator (152). Thus, as translation post (158) is rotated around the circular path defined by translator (152), translation post (158) will drive cutter (30) between maximum and minimum axial translation speeds based on the shape of translator (152). Accordingly, the axial translation speed of cutter (30) can generally be expressed graphically using a sine wave, with axial displacement on the x-axis and axial speed on the y-axis. In some circumstances, this variable axial translation speed may be desirable to both reduce wear on biopsy device (10) and reduce vibrations experienced by an operator. In use, the slower axial translation of cutter (30) will correspond to cutter (30) being positioned proximally and distally relative to lateral aperture (24). Meanwhile, the fastest axial translation of cutter (30) will correspond to cutter (30) being positioned at an intermediate position between the distal and proximal ends of lateral aperture (24).

It should be understood that the distal position of cutter (30) shown in FIG. 7C, corresponds to a position where cutter (30) has severed a tissue sample. To promote transportation of the severed tissue sample through cutter (30), in some examples cutter drive mechanism (100) may stop for a predetermined period of time to optimize transport of the tissue sample through cutter (30). In other examples, cutter (30) can immediately begin to retract proximally. Regardless of whether cutter drive mechanism (100) pauses or not, at some predetermined point, it may be desirable to retract cutter (30) proximally to sever another tissue sample. To retract cutter (30) proximally, rotation of cutter drive mechanism (100) continues as described above. This causes translator (152) to continue rotating as shown in FIG. 7D. Again, rotation of translator (152) causes translation post (158) to be displaced transversely and longitudinally. The longitudinal displacement of translation post (158) now pulls coupler (160) proximally via connector (170). Connector (170) thereby acts on cutter driver (130) to translate cutter (30) proximally. This rotation continues until translator (152) returns to the position shown in FIG. 7A.

Although cutter (30) could be retracted by reversing the direction of rotation of actuators (116, 118), in some examples it is desirable to rotate actuators (116, 118) in a single rotation direction. For instance, as described above, actuators (116, 118) are driven by cable (14), which can be constructed as a rotary drive cable. As such, it may be desirable to only provide rotation through cable (14) in a single direction to reduce the occurrence of cable whip or other phenomenon associated with rapid torque changes within cable (14). Additionally, although the use described herein involves counterclockwise rotation of actuators (116, 118), it should be understood that in other uses, actuators (116, 118) can be readily rotated through a clockwise direction to accomplish the same translational pattern of cutter (30).

III. Exemplary Alternative Cutter Drive Mechanism with Spool Drive

FIGS. 8-12 show an exemplary alternative cutter drive mechanism (200) that can be readily incorporated into body (12) of biopsy device (10) to drive rotation and translation of cutter (30). Cutter drive mechanism (200) is generally configured to simultaneously rotate and translate cutter (30) through a predetermined movement pattern with a rotary input from cable (14) in a single rotation direction. As will be described in greater detail below, the predetermined movement pattern of cutter (30) generally involves cutter (30) rotating continuously in a single direction while cutter (30) also translates first distally and then proximally. Accordingly, it should be understood that as a consequence of this configuration, it is not necessary to reverse the rotary input of cable (14) to translation cutter (30) from distal translation to proximal translation.

Figure 9:
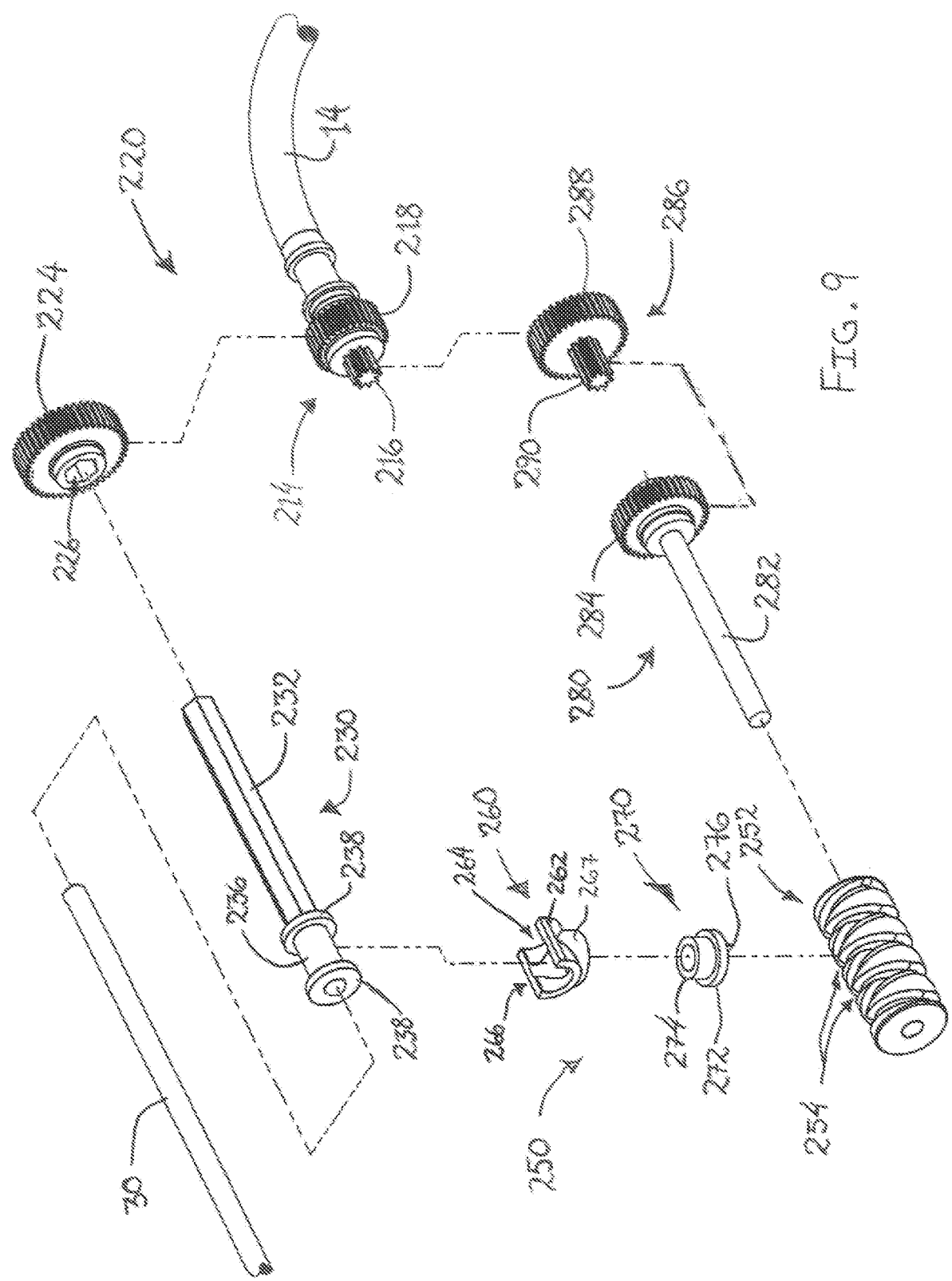
FIG. 9 depicts an exploded perspective view of the cutter drive mechanism of FIG. 8.

Cutter drive mechanism (200) comprises an input assembly (210), a rotation assembly (220), and a translation assembly (250). As best seen in FIG. 9, input assembly (210) is generally configured to couple to cable (14) to provide mechanical power to both rotation assembly (220) and translation assembly (250). Although not shown, it should be understood that in some examples input assembly (210) can include a rotatory coupler similar to rotary coupler (112) described above that is configured to permit cable (14) to selectively couple to input assembly (210). As with rotary coupler (112), it should be understood that a suitable rotary coupler can include a variety of features to support selective coupling of cable (14), By way of example only, suitable features may include gears, bearings, fasteners, and/or etc.

It should be understood that in the present example cable (14) is not permanently attached to input assembly (210). Instead, cable (14) can be selectively decoupled from input assembly (210) when biopsy device (10) is not in use. In some circumstances this feature is desirable to promote flexibility, ease of use, and ease of storage of biopsy device (10). Thus, it should be understood that this feature is merely optional and that in some examples cable (14) is permanently coupled to indexing assembly (210).

Input assembly (210) further includes a driver (214) extending distally from cable (14). Driver (214) is generally configured to transfer rotary motion of cable (14) to various components of input assembly (210) as will be described in greater detail below. Driver (214) includes a translation actuator (216) and a rotation actuator (218). In the present example, actuators (216, 218) are of integral construction with driver (214). However, it should be understood that in other examples actuators (216, 218) can be separate from driver (214) and attached thereto by various fastening techniques such as adhesive bonding, mechanical fastening, and/or etc.

Translation actuator (216) is disposed proximally relative to rotation actuator (218) and is generally configured to engage various components of translation assembly (250). In the present example, translation actuator (216) is shown as a spur gear. However, as will be described in greater detail below, it should be understood that various alternative actuators can be used as will be appreciated by those of ordinary skill in the art.

Rotation actuator (218) is positioned distally relative to translation actuator (216) at the proximal end of driver (214). Rotation actuator (218) is generally configured to engage various components of rotation assembly (220) as will be described in greater detail below. In the present example, rotation actuator (218) is shown as a spur gear and defines a larger pitch diameter relative to a pitch diameter of translation actuator (216). The differing pitch diameters of translation actuator (216) and translation actuator (216) can provide differing power outputs to rotation assembly (220) and/or translation assembly (250). For instance, in the present example the relatively large pitch diameter of rotation actuator (218) provides less power, but more speed. Similarly, the relatively small pitch diameter of translation actuator (216) provides less speed, but more power. However, as will be described in greater detail below, it should be understood that various alternative actuators can be used as will be appreciated by those of ordinary skill in the art.

Rotation assembly (220) is best seen in FIG. 9. As can be seen, rotation assembly (220) comprises a keyed actuator (224), and a cutter driver (230). Keyed actuator (224) is generally configured to provide rotation from driver (214) to cutter driver (230) to ultimately rotate cutter (30). In the present example, keyed actuator (224) is shown as a spur gear that directly meshes with rotation actuator (218). Although keyed actuator (224) meshes directly with rotation actuator (218) in the present example, it should be understood that in other examples rotation assembly (220) can include one or more intermediate actuators or gears similar to intermediate actuator (122) described above.

Keyed actuator (224) additionally defines a bore (226) extending therethrough. Bore (226) is generally sized to accommodate the combination of cutter driver (230) and cutter (30) such that keyed actuator (224) is generally coaxial with cutter (30). Bore (226) is further configured to transfer rotation of keyed actuator (224) to cutter driver (30), while also permitting at least some translation of cutter driver (30) relative to keyed actuator (224). To transfer rotation of keyed actuator (224) to cutter driver (230) while still allowing translation of cutter driver (230) relative to keyed actuator (224), keyed actuator (224) is generally "keyed" to rotatably engage cutter driver (230).

Although the term "keyed" may be understood by some to convey a particular structure, it should be understood that no such limitation is intended. For instance, in the present example bore (226) defines a generally hexagonal cross-sectional shape to make keyed actuator (224) "keyed." However, it should be understood that in other examples a variety of alternative shapes and configurations can be used. For instance, in some examples bore (226) can define a square, triangular, oval-shaped, octagonal, or other suitable cross-sectional shapes. Alternatively, in other examples bore (226) can be cylindrical in shape with an additional square or rectangular key included within keyed actuator (224) to correspond to a mating channel included within cutter driver (230). Of course, various other "keyed" configurations can be used as will be apparent to those of ordinary skill in the art in view of the teachings herein.

Cutter driver (230) is best seen in FIG. 9. As will be described in greater detail below, cutter driver (230) engages with both rotation assembly (220) and translation assembly (250) to manipulate cutter (30) during a biopsy procedure. Cutter driver (230) is generally overmolded or otherwise fixedly secured to cutter (30). To engage rotation assembly (220), cutter driver (230) includes a rotation portion (232). Rotation portion (232) defines a generally hexagonal cross-sectional shape that corresponds to the hexagonal shape of bore (226) in keyed actuator (224). Rotation portion (232) generally extends for a length that corresponds to the range of translation of cutter (30). In some examples, this range of motion generally corresponds to the length of lateral aperture (24), although other suitable ranges of motion can be used.

As will be described in greater detail below, cutter driver (230) is also configured to engage at least a portion of translation assembly (250). To permit this engagement, cutter driver (230) includes translation portion (234) disposed distally of rotation portion (232). Translation portion (234) includes a cylindrical receiver (236) disposed between two stops (238). Cylindrical receiver (236) defines a generally cylindrical shape that is configured to receive a portion of translation assembly (250) as will be described in greater detail below. Each stop (238) in the present example is configured as a flange extending outwardly from cylindrical receiver (236) on each side of cylindrical receiver (236). As will be described in greater detail below, the combination of both stops (238) is generally configured to permit at least a portion of translation assembly (250) to translate cutter (30) via cutter driver (230).

FIGS. 9 through 12 show translation assembly (250) in greater detail. As can be seen, translation assembly (250) is generally configured as a transverse spool system that includes a translator (252), a coupler (260), and a traveler (270). Translator (252) of the present example is configured as a self-reversing screw. As will be described in greater detail below, translator (252) is generally configured to translate cutter (30) in response to rotation of translation actuator (216) via various component of translation assembly (250). In the present configuration as a self-reversing screw, translator (252) is threaded such that traveler (270) can engage the threading and translate distally and then switch to proximal translation while translator (252) is rotated continuously in a single direction. As will be described in greater detail below, this movement of traveler (270) is readily transferred to cutter (30) thereby resulting in translation of cutter (30).

Figure 10:
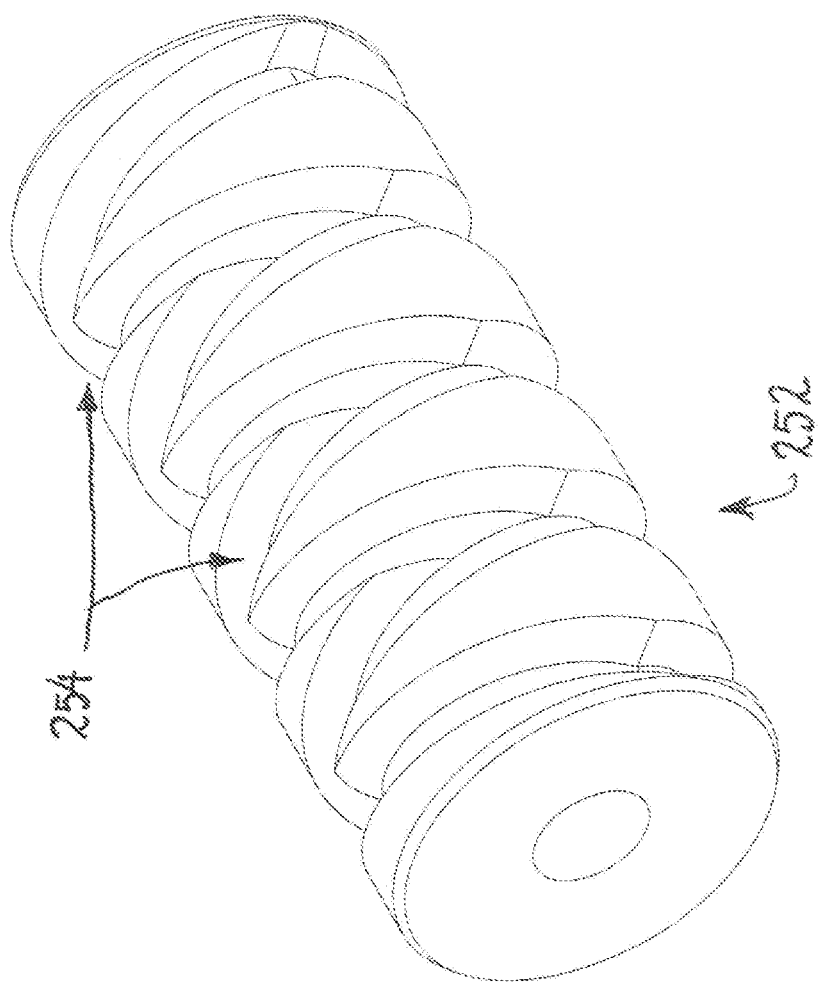
FIG. 10 depicts a perspective view of a translator of the cutter drive mechanism of FIG. 8.

As best seen in FIG. 10, translator (252) defines a plurality of threads (254) therein. Threads (254) are arranged in a symmetrical crossing pattern to provide two intermeshed drive paths along the surface of translator (252). As will be described in greater detail below, threads (254) are configured to receive a portion of traveler (270) to translate traveler (270) proximally and distally via rotation of translator (252). As will also be described in greater detail below, threads (254) are generally configured to automatically switch the translation direction of traveler (270) when traveler (270) reaches the proximal and distal end of translator (252) while translator (252) rotates continuously in a single direction.

Returning to FIG. 9, translator (252) is coupled to input assembly (210) by a rotation member (280) and an intermediate actuator (288). Rotation member (280) includes a shaft (282) and a gear (284) fixedly secured to shaft (282). Shaft (282) is generally solid and is configured for receipt within a bore in translator (252). In the present example, shaft (282) is fixedly secured to translator (252) such that rotation of shaft (282) results in corresponding rotation of translator (252). It should be understood that securement of shaft (282) to translator (252) can be accomplished by a variety of suitable ways such as a compression fit, adhesive bonding, and/or etc. In addition, or in the alternative, shaft (282) can be keyed to thereby avoid rotational slippage between shaft (282) and translator (252).

Gear (284) of rotation member (280) is fixedly secured to the proximal end of shaft (282). Thus, it should be understood that rotation of gear (284) results in corresponding rotation of shaft (282). Gear (284) of the present example is configured as a spur gear, although various alternative configurations can be used. As will be described in greater detail below, gear (284) is configured to mesh with intermediate actuator (286) to transfer rotation from input assembly (210) to translator (252).

Intermediate actuator (286) includes a proximal gear (288) and a distal gear (290). Both gears (288, 290) are configured as spur gears in the present examples, although various alternative configurations may be used. Proximal gear (288) is generally configured to mesh with translation actuator (216) of input assembly (210), while distal gear (290) is generally configured to mesh with gear (284) of rotation member (280). To obtain a desired gear ratio for rotation of translator (252), proximal gear (288) generally has larger pitch diameter relative to the pitch diameter of distal gear (290). As will be understood, this configuration generally results in translator (252) being rotated at a relatively slow rate (versus keyed actuator (224)), but with relatively high power.

Coupler (260) is best seen in 11 and 12. As can be seen, coupler (260) includes a semi-cylindrical body (262), and a receiving bore (268) extending downwardly from semi-cylindrical body (262). As will be understood, coupler (260) is generally configured to fasten to a portion of cutter driver (230) to translate cutter (30) through cutter driver (230) when coupler (260) is acted upon by translator (252) via traveler (270). To permit fastening of coupler (260) to cutter driver (230), semi-cylindrical body (262) defines a semi-cylindrical bore (264) generally corresponding to the outer diameter of cylindrical receiver (236) of cutter driver (230). Semi-cylindrical body (262) further defines an open portion (266) adjacent to, and in communication with, semi-cylindrical bore (264). As can be seen, the combination of semi-cylindrical bore (264) and open portion (266) makes semi-cylindrical body (262) just greater than half-cylindrical in shape. This additional cylindrical extension of semi-cylindrical body (262), permits the portion of semi-cylindrical body (262) adjacent to open portion (266) to grip cutter driver (230), thereby providing a snap fit configuration.

Receiving bore (268) of coupler (260) extends downward and laterally through semi-cylindrical body (262). Receiving bore (268) is generally configured to receive at least a portion of traveler (270) to permit coupling of travel (270) to cutter driver (230) via coupler (260). In the present example, a cylindrical spacer (267) is included extending away from semi-cylindrical body (262.) such that spacer (267) defines at least a portion of receiving bore (268), Spacer (267) is generally configured to provide at least some additional setoff distance between the end of receiving bore (268) and semi-cylindrical body (262) for alignment purposes. Thus, it should be understood that in some examples spacer (267) can have various lengths depending on the positioning of various components as will be understood in view of the teachings herein.

Figure 12:
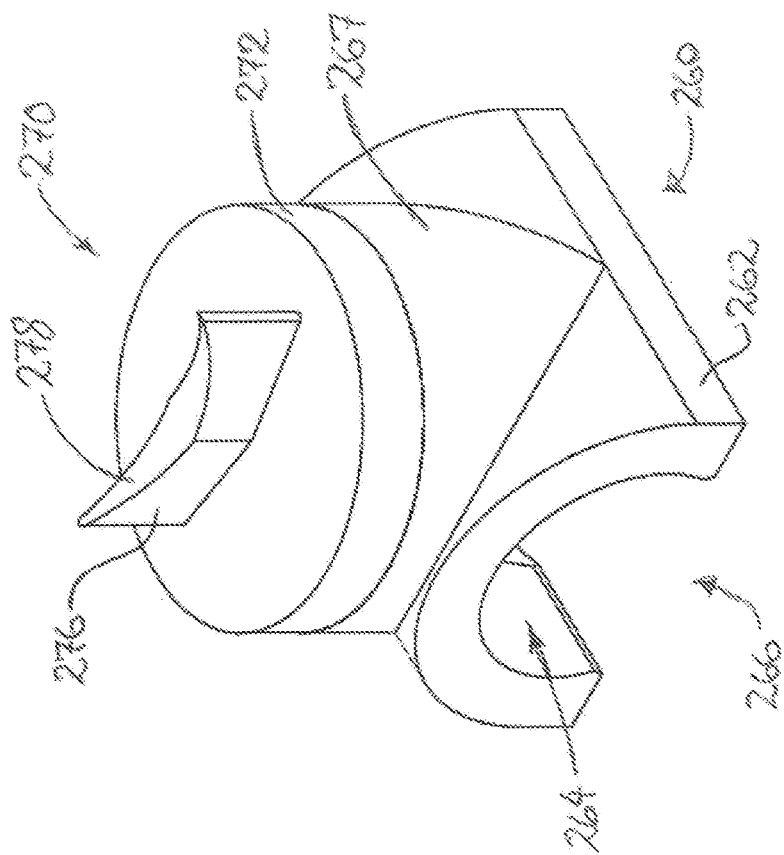
FIG. 12 depicts another perspective view of the coupler and traveler of FIG. 11.
Figure 11:
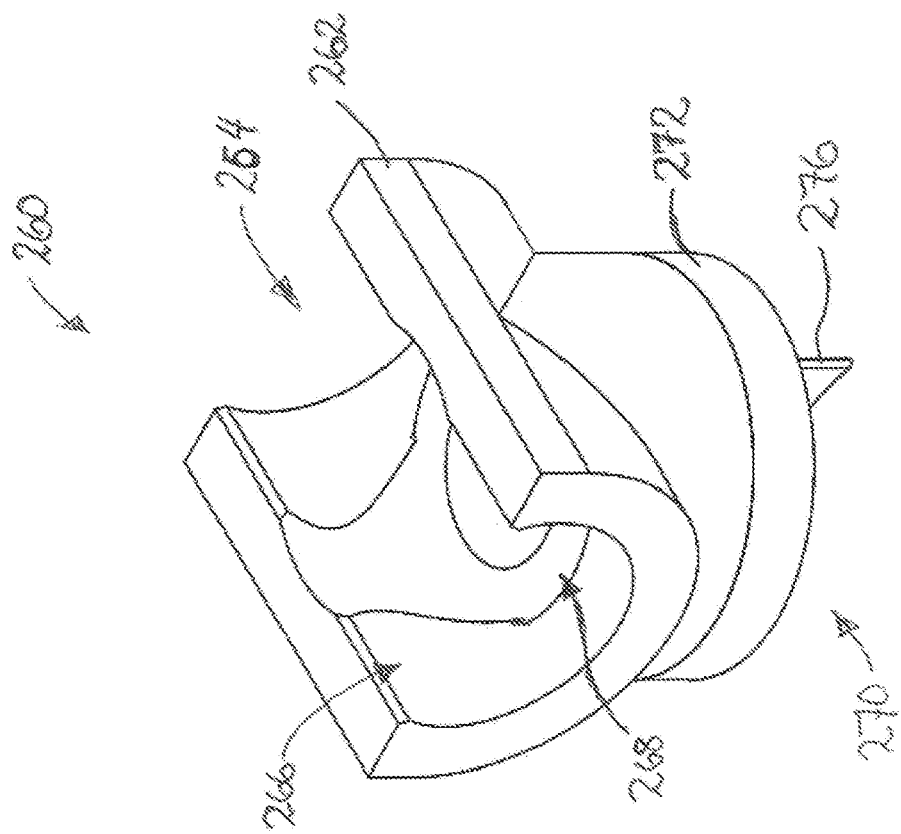
FIG. 11 depicts a perspective view of a coupler and traveler of the cutter drive mechanism of FIG. 8.

Traveler (270) is generally configured to mechanically couple translator (252) to coupler (260) to permit translator (252) to manipulate coupler (260). As can be seen in FIGS. 9 and 12, traveler (270) includes a cylindrical base (272) with a cylindrical protrusion (274) extending on one direction and an engagement tooth (276) extending in an opposite direction. Cylindrical protrusion (274) is generally configured for receipt within receiving bore (268) of coupler (260). As will be described in greater detail below, receiving bore (268) is generally configured to restrict lateral movement of cylindrical protrusion (274) relative to the axis defined by receiving bore (268) when cylindrical protrusion (274) is received therein. However, it should be understood that in some examples, receiving bore (268) can permit at least some rotational movement of cylindrical protrusion (274) to enhance alignment of traveler (270) with translator (252).

As best seen in FIG. 12, engagement tooth (276) extends from cylindrical base (272) defining a generally diamond-shaped cross-section. This diamond shape is generally configured to permit engagement tooth (276) to ride within threads (254) of translator (252). As will be described in greater detail below, certain portions of engagement tooth (276) are configured to engage threads (254) to facilitate translation of traveler (270) relative to translator (252) Engagement tooth (276) further defines a curved end (278). The shape of curved end (278) is generally semi-cylindrical with a diameter approximately equivalent to the minor diameter of translator (252) (e.g., the diameter at the low point of threads (254)). This shape is generally configured to promote rotation of translator (252) as engagement tooth (276) rides within threads (254) of translator (252).

Figure 13A:
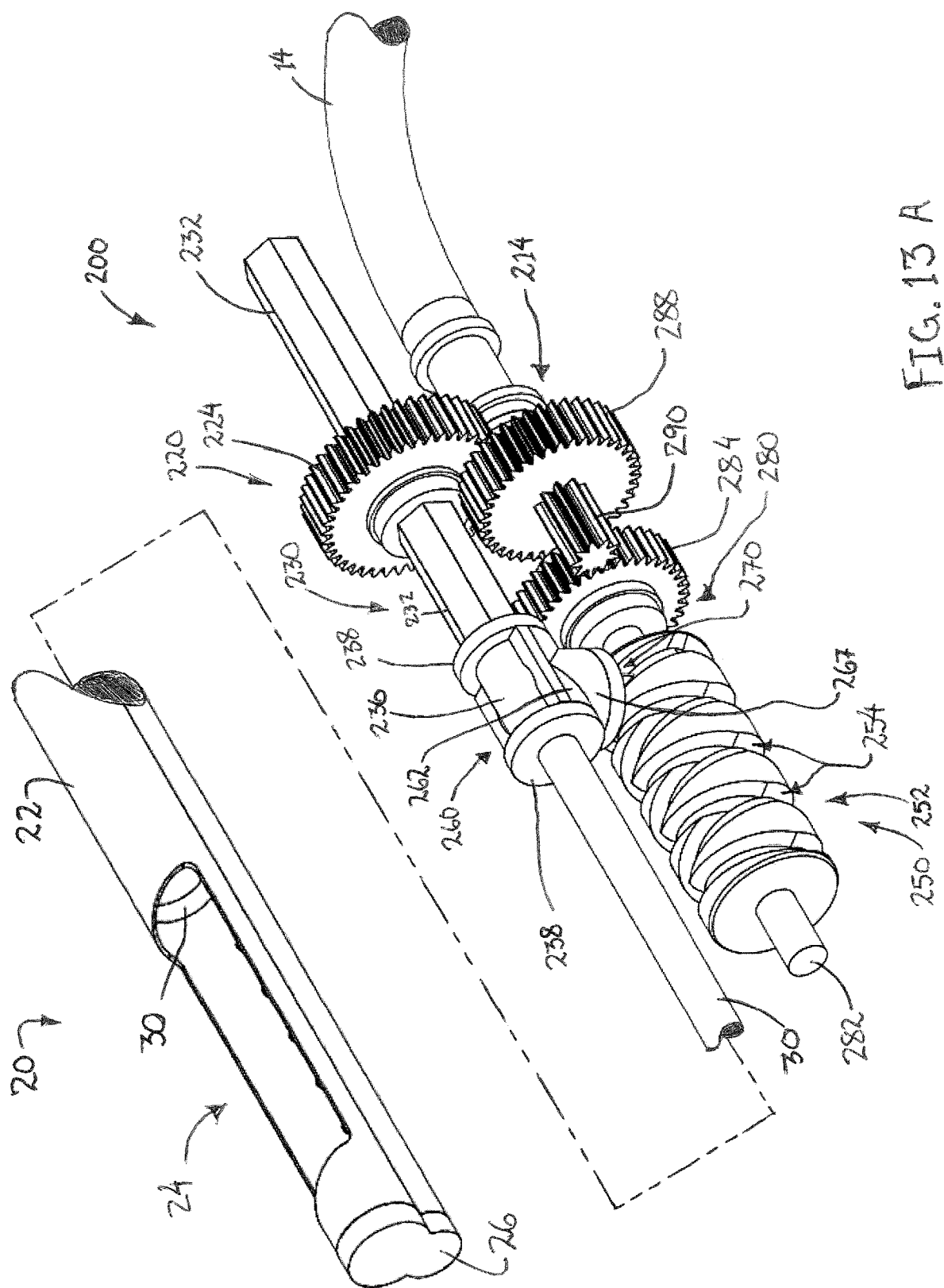
FIG. 13A depicts a perspective view of the cutter drive mechanism of FIG. 8, with the cutter drive mechanism in a retracted position.

FIGS. 13A through 14F show an exemplary use of cutter drive mechanism (200) to rotate and translate cutter (30). As seen in FIG. 13A, cutter drive mechanism (200) begins in an initial position. In the initial position, cutter (30) is retracted relative to the proximal end of lateral aperture (24). To achieve this position, translation actuator (216) is rotated so that translator (252) of translation assembly (250) also rotates. Meanwhile, engagement tooth (276) of traveler (270) rides within threads (254) of translator (252). This drives engagement tooth (276) proximally to the position shown in FIG. 13A. This in turn pulls cutter driver (230) proximally via coupler (260) and traveler (270), which results in cutter (30) being pulled proximally to the proximal position shown in FIG. 13A. It should be understood that translator (252) can generally be rotated in any direction (e.g., counter-clockwise, clockwise) to drive engagement tooth (276) through the cutter (30) actuation sequence described herein. However, it should be understood that to initially position engagement tooth (276) in the proximal position shown in FIG. 13A, it may be necessary to rotate translator (252) in a specific direction (e.g., if engagement tooth (276) is initially positioned at an intermediate position along the length of translator (252)). This is because threads (254) of translator (252) provide two different drive paths and once engagement tooth (276) is oriented in a specific drive path of threads (254) rotation of translator (252) in a specific direction may be required to generate translation of engagement tooth (276) in a specific direction.

Figure 13B:
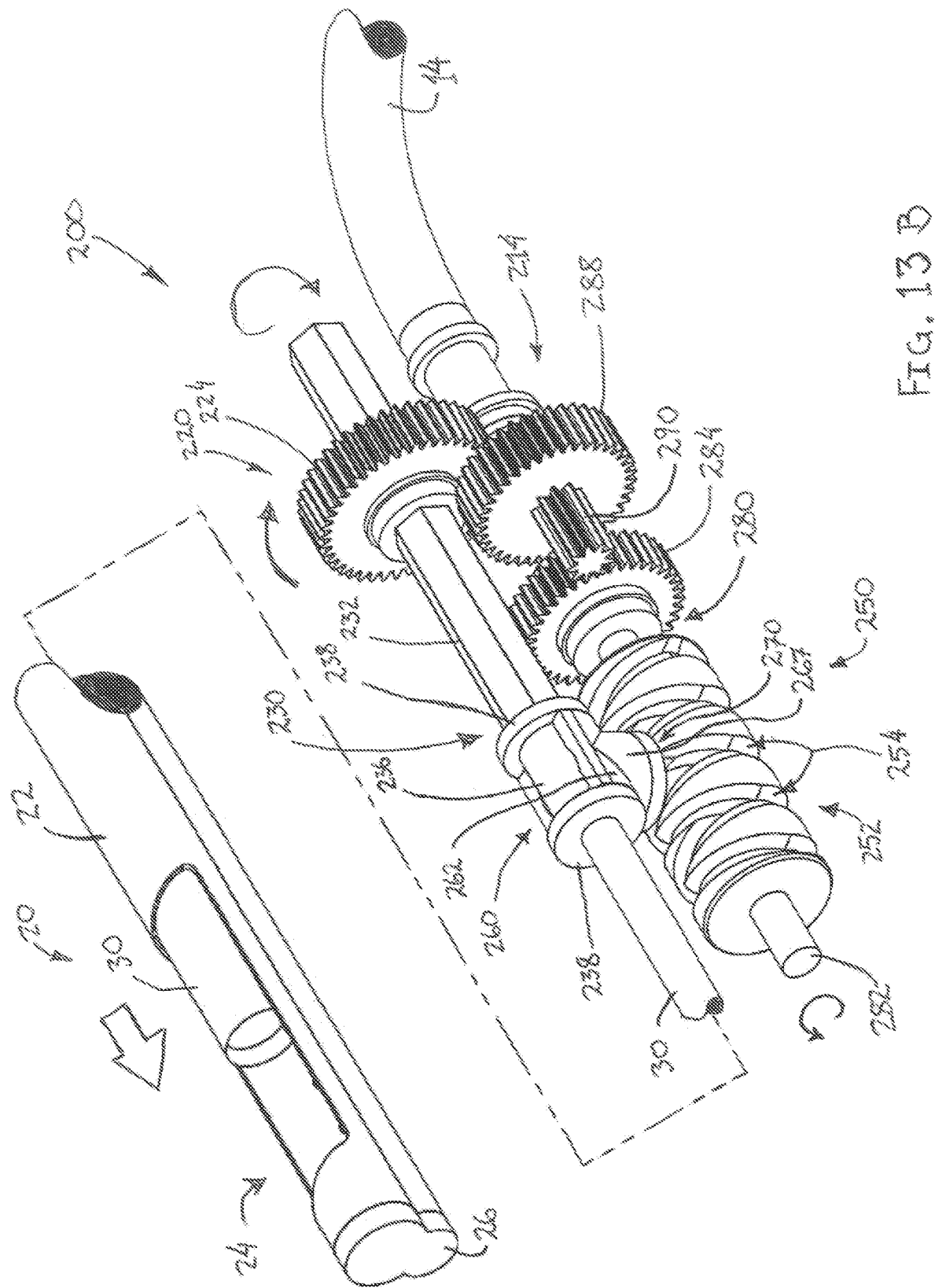
FIG. 13B depicts another perspective view of the cutter drive mechanism of FIG. 8, with the cutter drive mechanism in an intermediate position.

To advance cutter (30) distally, as shown in FIG. 13B, input assembly (210) rotates to rotate both translation actuator (216) and rotation actuator (218). Rotation of translation actuator (216) rotation of translator (252) via rotation member (280) and intermediate actuator (286). Rotation of translator (252) translates traveler (270) distally via engagement between threads (254) and engagement tooth (276). Distal translation of traveler (270) in turn translates coupler (260), which translates cutter driver (230) and cutter (30). Although translator (252) is shown in the present use as being rotated in a counter-clockwise direction (relative to the distal face of translator (252) shown in FIG. 13B), it should be understood that in other uses translator (252) can be rotated in the opposite clockwise direction. As described above, threads (254) are configured with two symmetrical drive paths that permit translator (252) drive traveler (270) proximally and distally while rotating continuously in a single direction. As a consequence of this configuration, translator (252) can operate in either rotation direction. However, it should be understood that once engagement tooth (276) of traveler (270) is engaged with a particular drive path of threads (254), a reversal in rotation of translator (252) will result in a reversal of the translation direction of traveler (270).

As translation actuator (216) rotates, rotation actuator (218) also rotates. Since rotation actuator (218) directly meshes with keyed actuator (224), this results in direct rotation of keyed actuator (224). Thus, keyed actuator (224) rotates as rotation actuator (218) rotates. The keyed relationship between keyed actuator (224) and cutter driver (230) results in rotation of cutter driver (230), even as cutter driver (230) is translated by translation assembly (250). Cutter (30) then rotates in via rotation cutter driver (230) by keyed actuator (224).

Figure 13C:
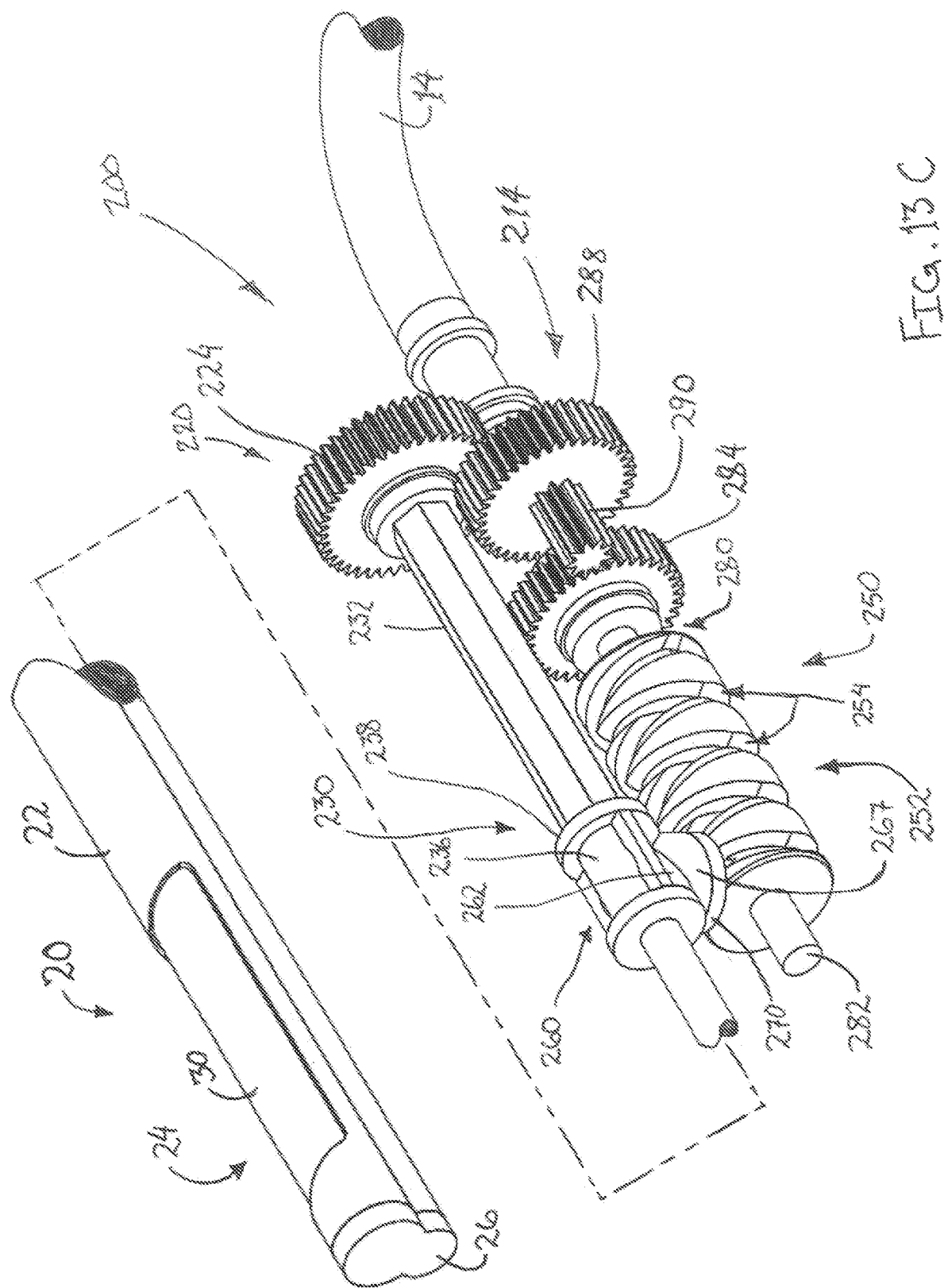
FIG. 13C depicts still another perspective view of the cutter drive mechanism of FIG. 8, with the cutter drive mechanism in an advanced position.

Rotation assembly (220) and translation assembly (250) continue to drive simultaneous cutter (30) rotation and translation until cutter (30) reaches the position shown in FIG. 13C. In the present use, this distal translation of cutter (30) corresponds to a cutting stroke where tissue received in lateral aperture (24) is severed using cutter (30).

At the completion of the cutting stroke, input assembly (210) may stop to stop rotation and translation of cutter (30). Such a stop may be merely temporary. Alternatively, input assembly (210) may continue rotating once the distal position shown in FIG. 13C is reached. Regardless, after cutter (30) reaches the distal position shown in FIG. 13C, it may be desirable to retract cutter (30) to the proximal position shown in FIG. 13A to prepare for receipt of another tissue sample within lateral aperture (24).

Figure 14B:
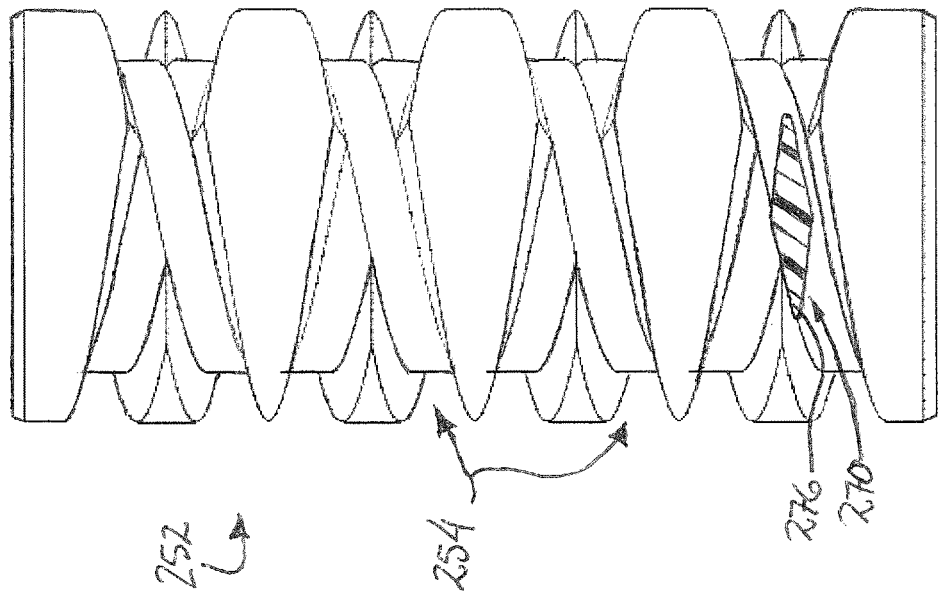
FIG. 14B depicts another top plan view of the traveler of FIG. 11 engaged with the translator of FIG. 10, with the traveler advancing further towards the reversal point.
Figure 14A:
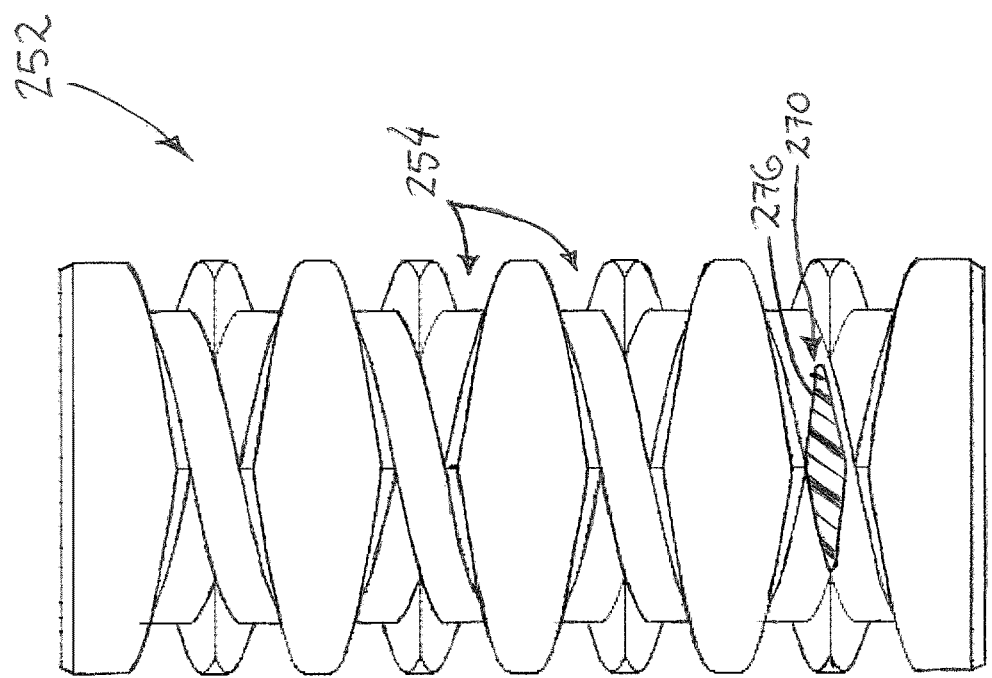
FIG. 14A depicts a top plan view of the traveler of FIG. 11 engaged with the translator of FIG. 10, with the traveler advancing towards a reversal point.

To retract cutter (30), the translation direction of traveler (270) should reverse. A sequence of the reversal of the translation direction of traveler (270) is shown in FIGS. 14A through 14F. In particular, FIGS. 14A and 14B show a progression of engagement tooth (276) as engagement tooth (276) approaches the reversal point. As can be seen, engagement tooth (276) is generally translated by sliding along the distal face of threads (254). The angle of attack of engagement tooth (276) relative to threads (254) permits translator (252) to pass engagement tooth (276) between gaps in threads (254) that are present to accommodate the dual drive paths defined by threads (254).

Figure 14D:
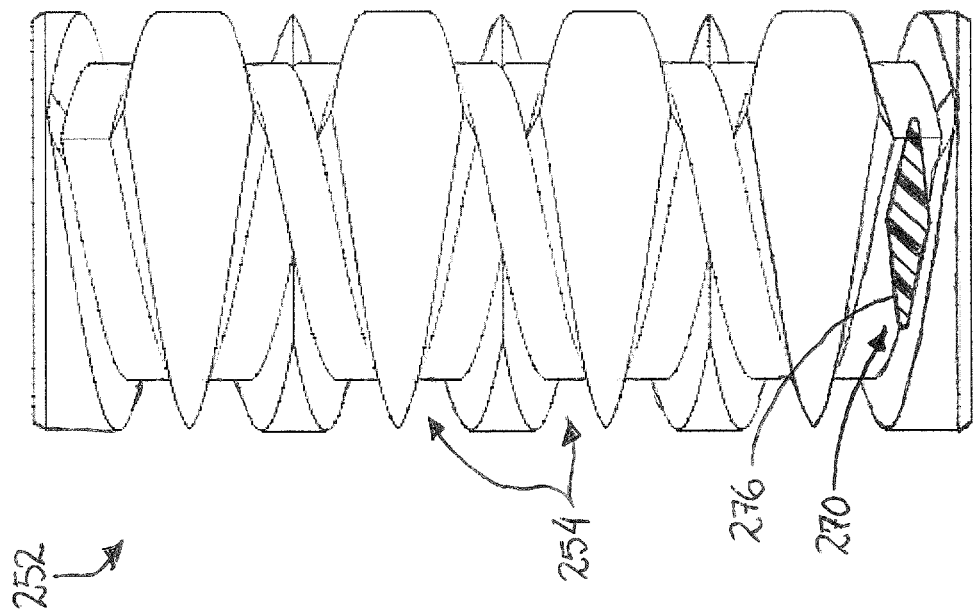
FIG. 14D depicts yet another top plan view of the traveler of FIG. 11 engaged with the translator of FIG. 10, with the traveler advanced past the reversal point.
Figure 14C:
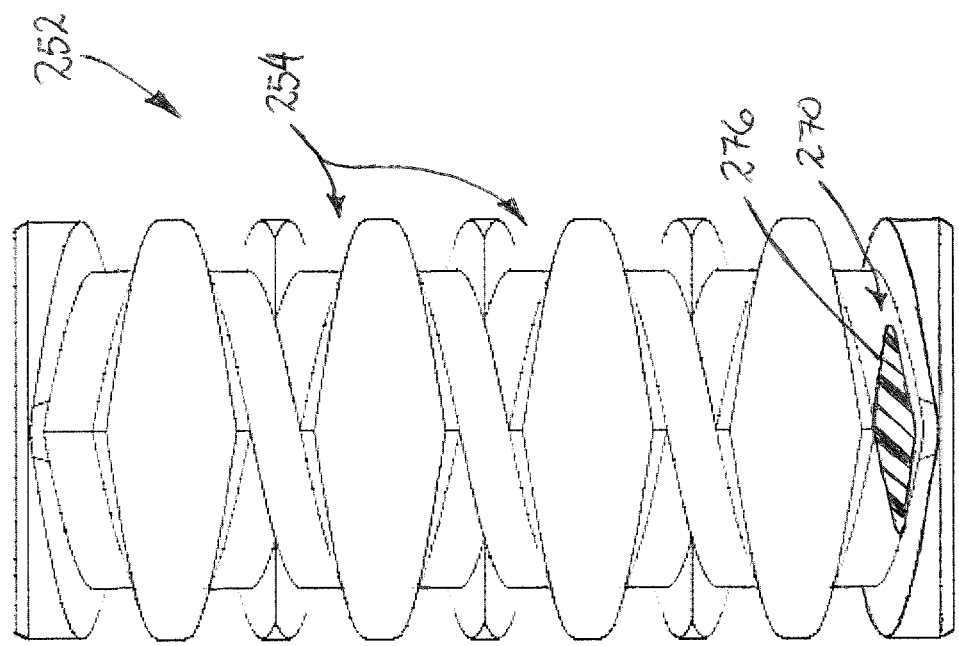
FIG. 14C depicts still another top plan view of the traveler of FIG. 11 engaged with the translator of FIG. 10, with the traveler disposed within the reversal point.
Figure 14F:
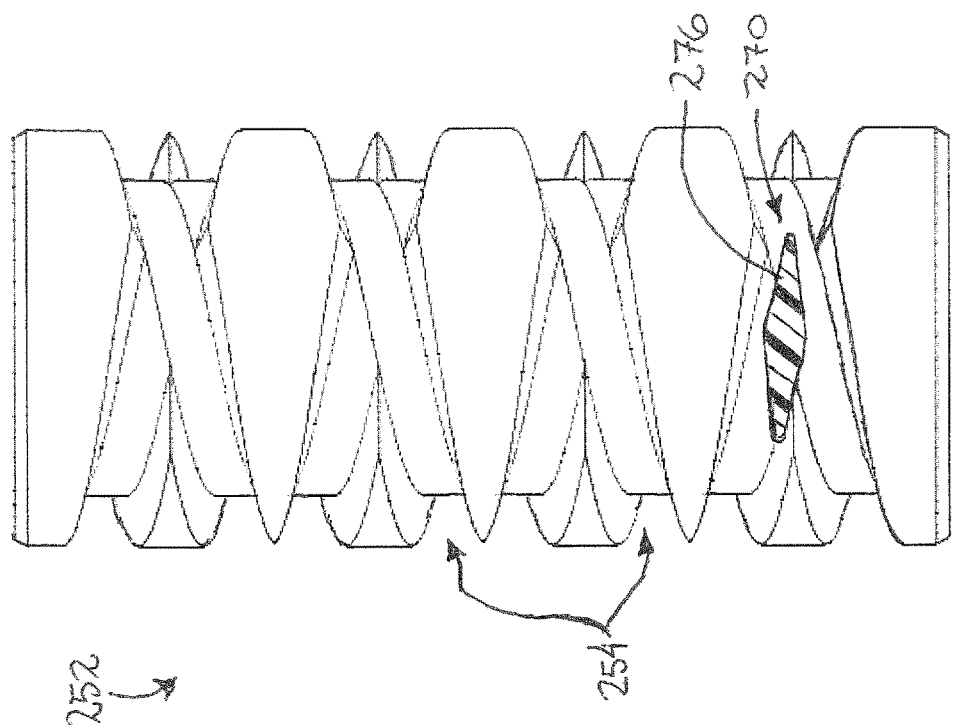
FIG. 14F depicts yet another top plan view of the traveler of FIG. 11 engaged with the translator of FIG. 10, with the traveler advanced even further past the reversal point.
Figure 14E:
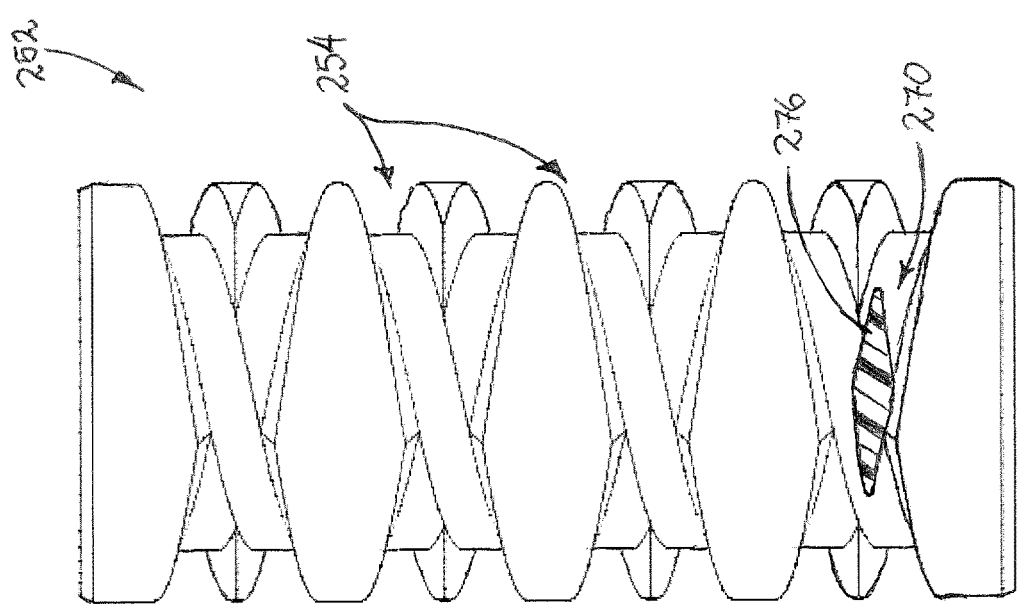
FIG. 14E depicts yet another top plan view of the traveler of FIG. 11 engaged with the translator of FIG. 10, with the traveler advanced further past the reversal point.

Engagement tooth (276) continues to slide along the distal face of threads (254) until engagement tooth (276) reaches the transition point shown in FIGS. 14C and 14D. As can be seen, at the transition point, engagement tooth (276) transitions from sliding on the distal face of threads (254) to sliding on the proximal face of threads (254). Once on the proximal face of threads (254), engagement tooth (276) begins to translate proximally instead of distally. Although not shown, it should be understood that in some examples engagement tooth (276) can also rotate slightly relative to the axis of semi-cylindrical bore (264) of coupler (260) so that the angle of attack of engagement tooth (276) matches the angle of the proximal face of threads (254). Once engagement tooth (276) is past the transition point, the proximal face of threads (254) pushes engagement tooth (276) proximally with engagement tooth (276) passing between each gap in threads (254) as shown in FIGS. 14E and 14F. Proximal translation of engagement tooth (276) (and cutter (30) via coupler (260) and traveler (270)) can then continue until cutter (30) is returned to the proximal position shown in FIG. 13A.

Although the transition point of engagement tooth (276) is described herein in connection with the distal position of cutter (30), it should be understood that a substantially same transition can occur in connection with the proximal position of cutter (30). Thus, once cutter (30) reaches the proximal position, the translation direction of cutter (30) is automatically transitioned to restart the cutting cycle. The cutting cycle described above can then be repeated indefinitely without ever reversing the rotation direction of input assembly (210). As described above, translation of cutter (30) without reversal of input assembly (210) can be desirable in certain contexts to avoid applying unnecessary torque to cable (14).

IV. Exemplary Alternative Cutter Drive Mechanism with Toggle Gear

Figure 16:
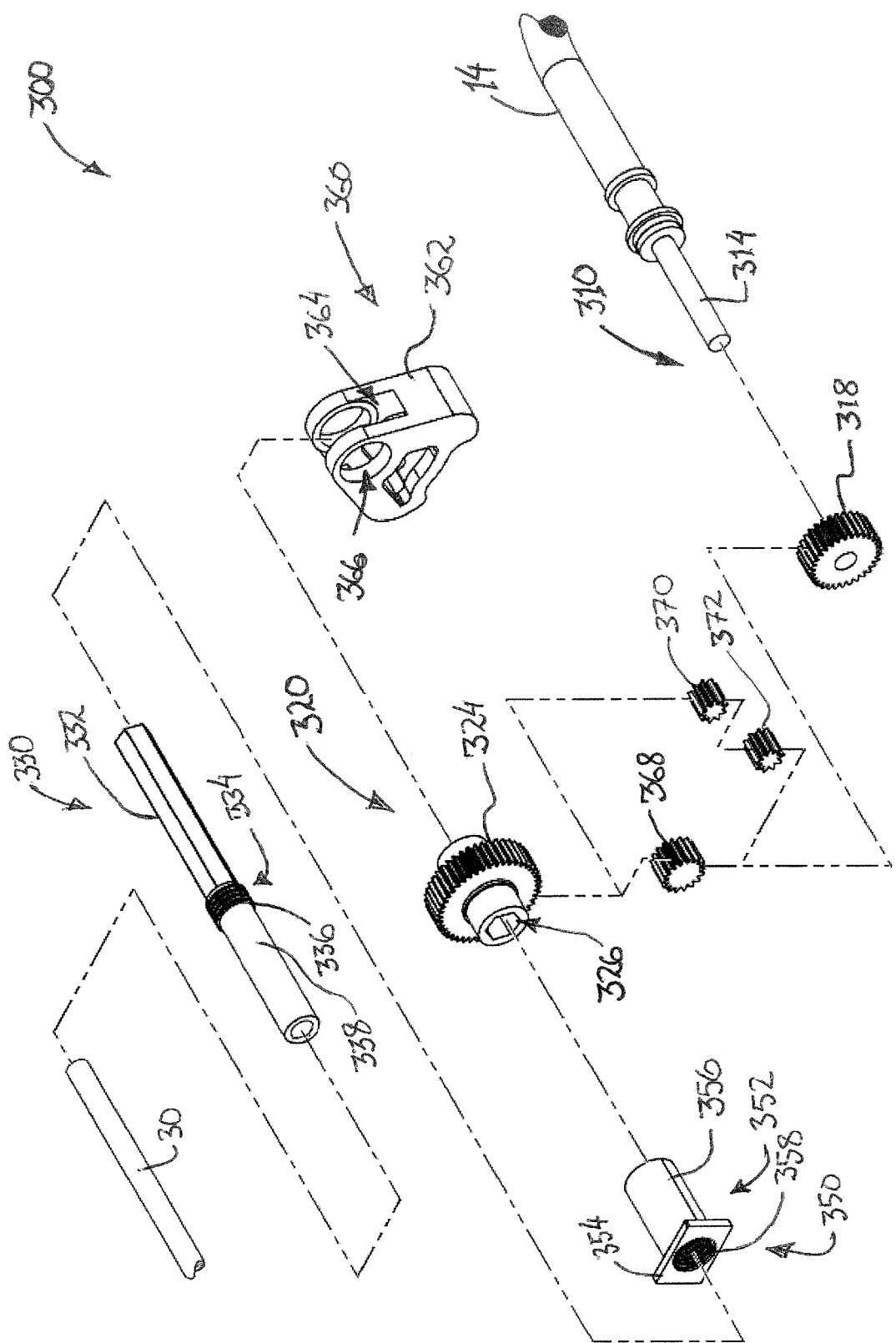
FIG. 16 depicts an exploded perspective view of the cutter drive mechanism of FIG. 15.
Figure 17:
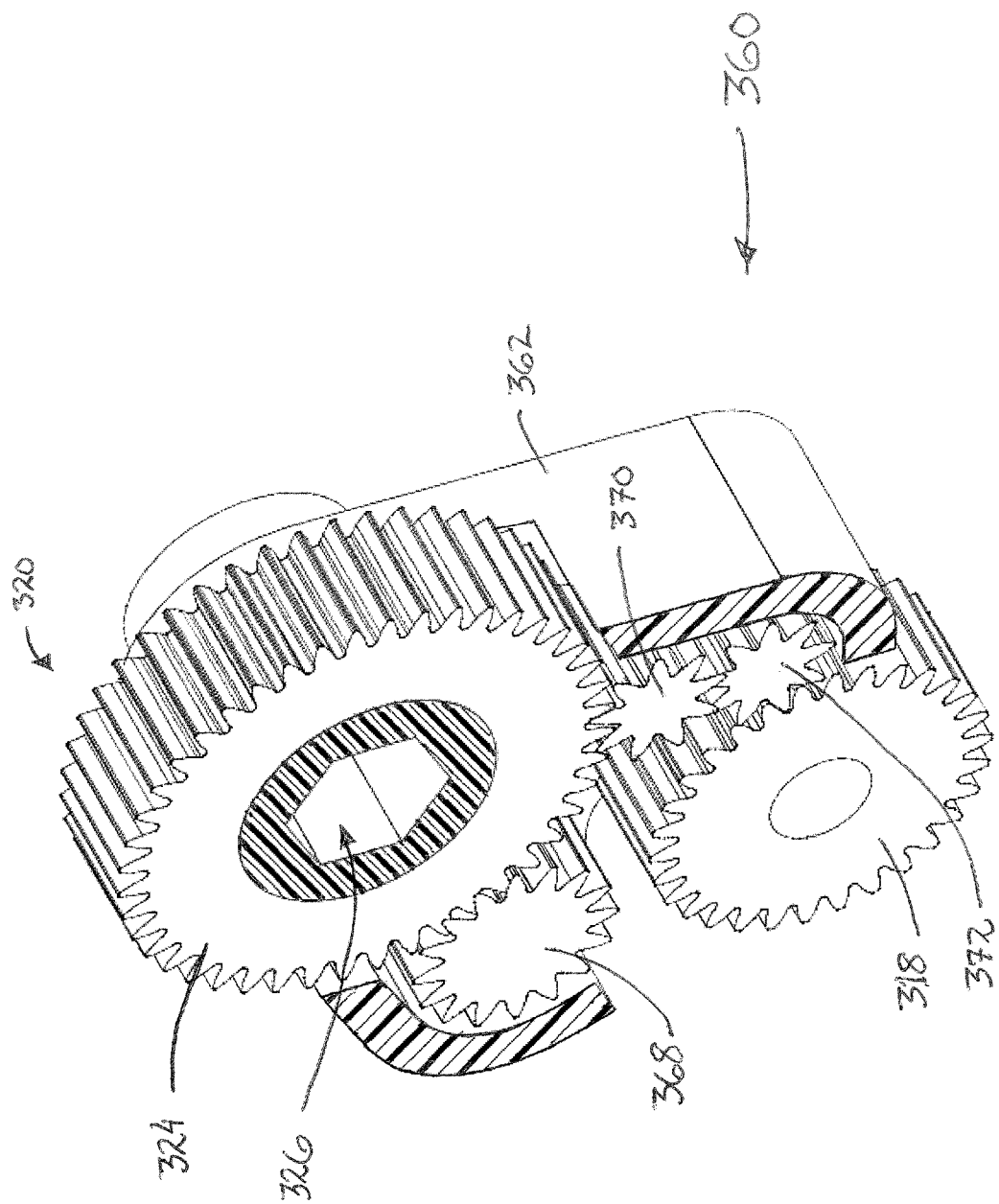
FIG. 17 depicts a perspective cross-sectional view of a gearbox assembly of the cutter drive mechanism of FIG. 15, the cross-section taken along line 17-17 of FIG. 15.

FIGS. 15-17 show an exemplary alternative cutter drive mechanism (300) that can be readily incorporated into body (12) of biopsy device (10) to drive rotation and translation of cutter (30). Cutter drive mechanism (300) is generally configured to simultaneously rotate and translate cutter (30) through a predetermined movement pattern with a rotary input from cable (14) in a single rotation direction. As will be described in greater detail below, the predetermined movement pattern of cutter (30) generally involves cutter (30) rotating continuously in a single direction while cutter (30) also translates first distally and then proximally. Accordingly, it should be understood that as a consequence of this configuration, it is not necessary to reverse the rotary input of cable (14) to translation cutter (30) from distal translation to proximal translation.

Cutter drive mechanism (300) comprises an input assembly (310), a rotation assembly (320), and a translation assembly (350). As best seen in FIG. 15, input assembly (310) is generally configured to couple to cable (14) to provide mechanical power to both rotation assembly (320) and translation assembly (350). Although not shown, it should be understood that in some examples input assembly (310) can include a rotary coupler similar to rotary coupler (112) described above that is configured to permit cable (14) to selectively couple to input assembly (310). As with rotary coupler (112), it should be understood that a suitable rotary coupler can include a variety of features to support selective coupling of cable (14). By way of example only, suitable features may include gears, bearings, fasteners, and/or etc.

It should be understood that in the present example cable (14) is not permanently attached to input assembly (310). Instead, cable (14) can be selectively decoupled from input assembly (310) when biopsy device (10) is not in use. In some circumstances this feature is desirable to promote flexibility, ease of use, and ease of storage of biopsy device (10). Thus, it should be understood that this feature is merely optional and that in some examples cable (14) is permanently coupled to indexing assembly (310).

Input assembly (310) further includes a driver (314) extending distally from cable (14). Driver (314) is generally configured to transfer rotary motion of cable (14) to various components of input assembly (310) as will be described in greater detail below. Driver (314) is secured to a rotation actuator (318), which is rotated by driver (314). In the present example, rotation actuator (318) is fixedly secured to driver (314) such that rotation actuator (318) rotates with driver (314). However, it should be understood that in other examples rotation actuator (318) can be separate from driver (314) and attached thereto by various fastening techniques such as adhesive bonding, mechanical fastening, and/or etc.

Rotation actuator (318) is positioned distally relative to cable (14) at the distal end of driver (314). Rotation actuator (318) is generally configured to engage various components of rotation assembly (320) as will be described in greater detail below. In the present example, rotation actuator (318) is shown as a spur gear. However, as will be described in greater detail below, it should be understood that various alternative actuators can be used as will be appreciated by those of ordinary skill in the art.

Rotation assembly (320) is best seen in FIG. 16. As can be seen, rotation assembly (320) comprises a keyed actuator (324), a gearbox assembly (360), and a cutter driver (330). Keyed actuator (324) is generally configured to provide rotation from driver (314) to cutter driver (330) to ultimately rotate cutter (30). In the present example, keyed actuator (324) is shown as a spur gear that indirectly meshes with rotation actuator (318). Although keyed actuator (324) meshes directly with gearbox assembly (360) in the present example, it should be understood that in other examples rotation assembly (320) can include one or more intermediate actuators or gears similar to intermediate actuator (122) described above disposed between keyed actuator (324) and gearbox assembly (360).

Keyed actuator (324) additionally defines a bore (326) extending therethrough. Bore (326) is generally sized to accommodate the combination of cutter driver (330) and cutter (30) such that keyed actuator (324) is generally coaxial with cutter (30). Bore (326) is further configured to transfer rotation of keyed actuator (324) to cutter driver (30), while also permitting at least some translation of cutter driver (30) relative to keyed actuator (324). To transfer rotation of keyed actuator (324) to cutter driver (330) while still allowing translation of cutter driver (330) relative to keyed actuator (324), keyed actuator (324) is generally "keyed" to rotatably engage cutter driver (330).

Although the term "keyed" may be understood by some to convey a particular structure, it should be understood that no such limitation is intended. For instance, in the present example bore (326) defines a generally hexagonal cross-sectional shape to make keyed actuator (324) "keyed." However, it should be understood that in other examples a variety of alternative shapes and configurations can be used. For instance, in some examples bore (326) can define a square, triangular, oval-shaped, octagonal, or other suitable cross-sectional shapes. Alternatively, in other examples bore (326) can be cylindrical in shape with an additional square or rectangular key included within keyed actuator (324) to correspond to a mating channel included within cutter driver (330). Of course, various other "keyed" configurations can be used as will be apparent to those of ordinary skill in the art in view of the teachings herein.

Cutter driver (330) is best seen in FIG. 16. As will be described in greater detail below, cutter driver (330) engages with both rotation assembly (320) and translation assembly (350) to manipulate cutter (30) during a biopsy procedure. Cutter driver (330) is generally overmolded or otherwise fixedly secured to cutter (30). To engage rotation assembly (320), cutter driver (330) includes a rotation portion (332). Rotation portion (332) defines a generally hexagonal cross-sectional shape that corresponds to the hexagonal shape of bore (326) in keyed actuator (324). Rotation portion (332) generally extends for a length that corresponds to the range of translation of cutter (30). In some examples, this range of motion generally corresponds to the length of lateral aperture (24), although other suitable ranges of motion can be used.

As will be described in greater detail below, cutter driver (330) is also configured to engage at least a portion of translation assembly (350). To permit this engagement, cutter driver (3A) includes translation portion (334) disposed distally of rotation portion (332). Translation portion (334) includes threading (336) disposed proximally of a zero-pitch region (338). Threading (336) is generally configured to mesh with corresponding components of translation assembly (350) as will be described in greater detail below. In some examples, zero pitch region (338) can be used to provide at least some rotation of cutter (30) without corresponding translation of cutter (30).

FIG. 16 shows translation assembly (350) in greater detail. As can be seen, translation assembly (350) is generally configured as a toggle gear system and includes a translator (352) that is configured to engage threading (336) of cutter driver (330). Translator (352) of the present example is generally configured as a nut. For instance, translator (352) includes a square-shaped gripping portion (354) and an elongate cylindrical receiver (356) with internal threading (358). Gripping portion (354) is configured for receipt in a portion of body (12). The square shape of gripping portion (354) permit body (12) to hold translator (352) in a fixed position relative to cutter (30) and cutter driver (330). Receiver (356) is configured to receive cutter driver (330) coaxially therein. As will be described in greater detail below, receipt of cutter driver (330) within receiver (356) permits internal threading (358) of receiver (356) to engage threading (336) of cutter driver (330) to thereby translate cutter driver (330) in response to rotation of cutter driver (330).

Gearbox assembly (360) can be seen in FIGS. 16 and 17. As can be seen, gearbox assembly (360) includes an outer housing (362), and a plurality of gears (368, 370, 372) received within a hollow interior (364) of outer housing (362). Outer housing (362) defines a generally triangular shape. At the apex of the triangular shape of outer housing (362), a receiving bore (366) extends through outer housing (362). Receiving bore (366) is generally sized to receive at least a portion of keyed actuator (324) to hold keyed actuator (324) within outer housing (352). Receiving bore (366) is additionally sized such that the combination of cutter driver (330) and cutter (30) can pass through outer housing (362).

Three gears (368, 370, 372) are disposed within outer housing (352). In particular, gears (368, 370, 372) include a first stage rotation gear (368), a second stage rotation gear (370), and a reversing gear (372). As will be described in greater detail below, each rotation gear (368, 370) is generally configured to mesh with keyed actuator (324) at different stages during a biopsy procedure to selectively control the rotation direction of keyed actuator (324). As will be understood, such selective control over the rotation direction of keyed actuator (324) may be desirable to switch the translation direction of cutter (30).

First stage rotation gear (368) is configured as a spur gear, which is configured to mesh with both rotation actuator (318) and keyed actuator (324) independently of second stage rotation gear (370). Second stage rotation gear (368) is similarly configured as a spur gear, which is configured to mesh with keyed actuator (324). However, unlike first stage rotation gear (368), second stage rotation gear (370) is configured to mesh with reversing gear (372). Reversing gear (372) then meshes with rotation actuator (318). It should be understood that this configuration permits second stage rotation gear (370) to rotate in a different rotational direction relative to first stage rotation gear (368) even though both first stage rotation gear (368) and second stage rotation gear (370) are powered by rotation actuator (318) while rotation actuator (318) rotates in a single direction.

FIGS. 18A and 18B show an exemplary use of cutter drive mechanism (300) to provide translation of cutter (30) in two directions even when cable (14) provides a rotatory input in a single direction. As seen in FIG. 14, rotation of rotation actuator (318) is in the counterclockwise direction (distal direction into the page). It should be understood that this rotation direction is shown as an example only and that cutter drive mechanism (300) operates in a similar manner when rotation actuator (318) is rotated in the opposite clockwise direction. Regardless of the particular rotation direction for rotation actuator (318), gearbox assembly (360) is initially in a second stage with rotation actuator (318) is initially meshed with reversing gear (372). This causes rotation of reversing gear (372) in the opposite direction (e.g., clockwise) relative to rotation actuator (318). Reversing gear (372) is also meshed with second stage rotation gear (370). Meshing between reversing gear (372) and second stage rotation gear (370) causes second stage rotation gear (370) to rotate in an opposite direction (e.g., counterclockwise) relative to the rotation direction of reversing gear (372). Second stage rotation gear (370) is also meshed with keyed actuator (324). Meshing between second stage rotation gear (370) and keyed actuator (324) causes keyed actuator (324) to rotate in an opposite direction (e.g., clockwise) relative to the rotation direction of second stage rotation gear (370).

Rotation of keyed actuator (324) causes cutter driver (330) and cutter (30) to rotate. Simultaneously, due to engagement between internal threading (358) of translator (352) and threading (336) of cutter driver (330), cutter (30) also translates in the proximal or distal direction depending on the particular orientation of threading (336, 358). In some uses, the second stage position of gearbox assembly (360) shown in FIG. 18A may correspond to cutter (30) being translated distally relative to lateral aperture (24). Of course, it should be understood that in other uses the second stage position can also correspond to cutter being translated proximally, if, for example, rotation actuator (318) is rotated in an opposite direction.

At various stages during a biopsy procedure it may be desirable to reverse the translation direction of cutter (30). For example, after cutter (30) has been translated to a distal position relative to lateral aperture (24), it may be desirable to reverse the translation of cutter (30) to return cutter (30) to a proximal position relative to lateral aperture (24). This sequence, for example, can permit cutter (30) to open lateral aperture (24) for collection of another tissue sample. Regardless of the particular reason for reversing cutter (30) translation, the translation direction can be reversed by pivoting outer housing (362) of gearbox assembly (360) to a first stage position as shown in FIG. 18B. In this position, second stage rotation gear (370) and reversing gear (372) have been moved away from rotation actuator (318) such that reversing gear (372) no longer meshes with rotation actuator (318). Instead, now first stage rotation gear (368) now meshes with rotation actuator (318). This causes rotation of first stage rotation gear (368) to rotate in an opposite direction (e.g., clockwise) relative to the rotation direction of rotation actuator (318).

First stage rotation gear (368) is also meshed with keyed actuator (324). This causes first stage rotation gear (368) to rotate keyed actuator (324) in an opposite direction (e.g., counterclockwise) relative to the rotation direction of first stage rotation gear (368). Thus, even though rotation actuator (318) rotates in the same direction as described above with respect to FIG. 18A and the second stage position, keyed actuator (324) now rotates in an opposite direction. This rotation of keyed actuator (324) in an opposite direction in turn causes translation of cutter (30) in an opposite direction due to engagement between internal threading (358) of translator (352) and threading (336) of cutter driver (330).

Exemplary Alternative Cutter Drive Mechanism with Bevel Gear

Figure 19:
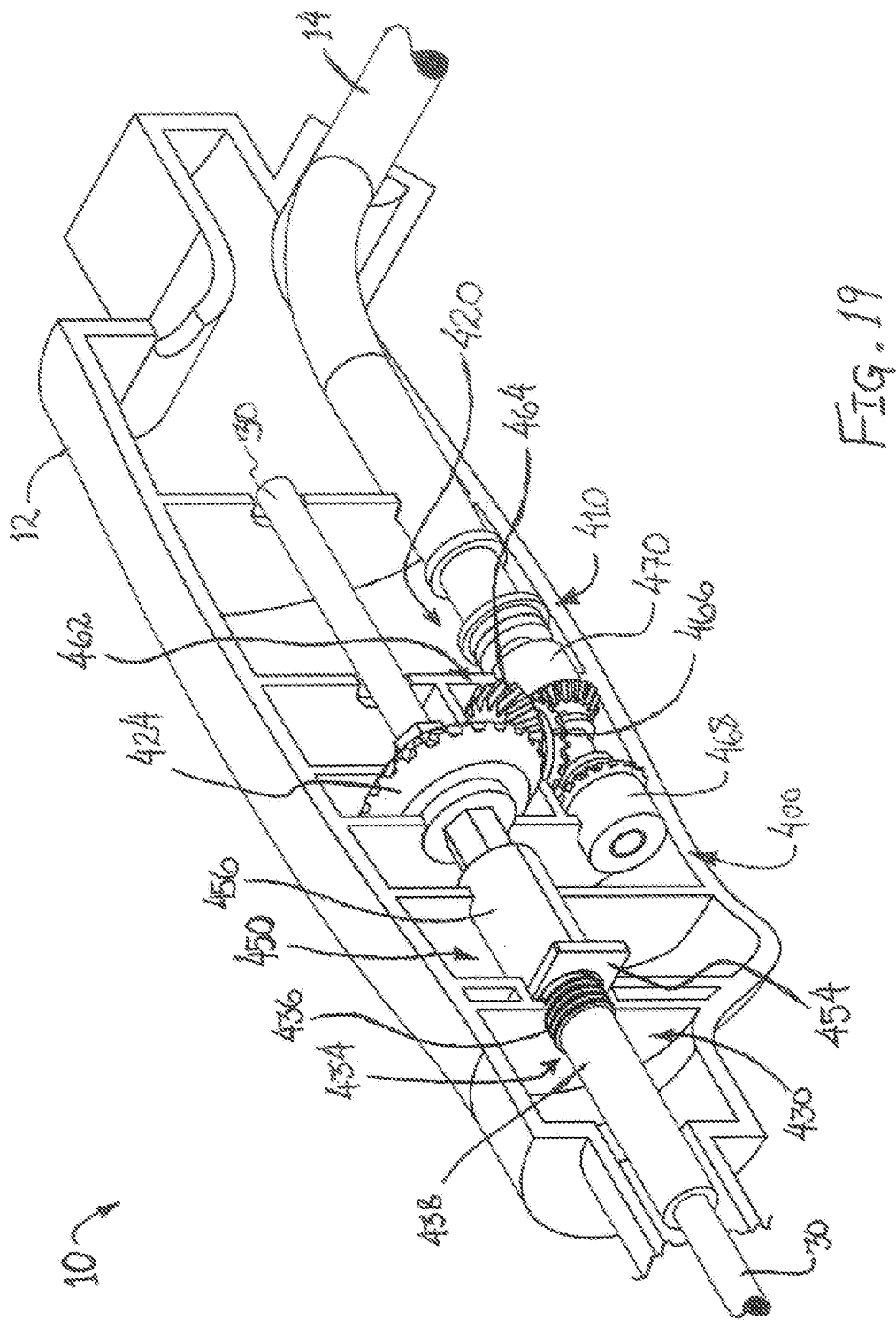
FIG. 19 depicts a perspective view of still another exemplary alternative cutter drive mechanism for incorporation into the biopsy device of FIG. 1.

FIGS. 19 and 20 show an exemplary alternative cutter drive mechanism (400) that can be readily incorporated into body (12) of biopsy device (10) to drive rotation and translation of cutter (30). Cutter drive mechanism (400) is generally configured to simultaneously rotate and translate cutter (30) through a predetermined movement pattern with a rotary input from cable (14) in a single rotation direction. As will be described in greater detail below, the predetermined movement pattern of cutter (30) generally involves cutter (30) rotating continuously in a single direction while cutter (30) also translates first distally and then proximally. Accordingly, it should be understood that as a consequence of this configuration, it is not necessary to reverse the rotary input of cable (14) to translation cutter (30) from distal translation to proximal translation.

Cutter drive mechanism (400) comprises an input assembly (410), a rotation assembly (420), and a translation assembly (450). As best seen in FIG. 20, input assembly (410) is generally configured to couple to cable (14) to provide mechanical power to both rotation assembly (420) and translation assembly (450). Although not shown, it should be understood that in some examples input assembly (410) can include a rotatory coupler similar to rotary coupler (112) described above that is configured to permit cable (14) to selectively couple to input assembly (410). As with rotary coupler (112), it should be understood that a suitable rotary coupler can include a variety of features to support selective coupling of cable (14). By way of example only, suitable features may include gears, bearings, fasteners, and/or etc.

It should be understood that in the present example cable (14) is not permanently attached to input assembly (410). Instead, cable (14) can be selectively decoupled from input assembly (410) when biopsy device (10) is not in use. In some circumstances this feature is desirable to promote flexibility, ease of use, and ease of storage of biopsy device (10). Thus, it should be understood that this feature is merely optional and that in some examples cable (14) is permanently coupled to indexing assembly (410).

Input assembly (410) further includes a driver (414) extending distally from cable (14). Driver (414) is generally configured to transfer rotary motion of cable (14) to various components of rotation assembly (420) as will be described in greater detail below. Driver (414) of the present example comprises an elongate shaft that is configured to receive various rotational components of rotation assembly (420). As will be described in greater detail below, driver (414) can also be configured to permit at least some components of rotation assembly (420) to slide or translate relative to driver (414) while still transferring rotary motion to rotation assembly (420). Thus, although not shown, it should be understood that in some examples driver (414) can include keyed features such as an irregular shape, a keyway, a key, and/or etc.

Rotation assembly (420) is best seen in FIG. 20. As can be seen, rotation assembly (420) comprises a keyed actuator (424), a reversal assembly (460), and a cutter driver (430). Keyed actuator (424) is generally configured to provide rotation from driver (414) to cutter driver (430) to ultimately rotate cutter (30). In the present example, keyed actuator (424) is shown as a bevel gear that meshes with portions of reversal assembly (460).

Keyed actuator (424) additionally defines a bore (426) extending therethrough. Bore (426) is generally sized to accommodate the combination of cutter driver (430) and cutter (30) such that keyed actuator (424) is generally coaxial with cutter (30). Bore (426) is further configured to transfer rotation of keyed actuator (424) to cutter driver (30), while also permitting at least some translation of cutter driver (30) relative to keyed actuator (424). To transfer rotation of keyed actuator (424) to cutter driver (430) while still allowing translation of cutter driver (430) relative to keyed actuator (424), keyed actuator (424) is generally "keyed" to rotatably engage cutter driver (430).

Although the term "keyed" may be understood by some to convey a particular structure, it should be understood that no such limitation is intended. For instance, in the present example bore (426) defines a generally hexagonal cross-sectional shape to make keyed actuator (424) "keyed," However, it should be understood that in other examples a variety of alternative shapes and configurations can be used.

For instance, in some examples bore (426) can define a square, triangular, oval-shaped, octagonal, or other suitable cross-sectional shapes. Alternatively, in other examples bore (426) can be cylindrical in shape with an additional square or rectangular key included within keyed actuator (424) to correspond to a mating channel included within cutter driver (430). Of course, various other "keyed" configurations can be used as will be apparent to those of ordinary skill in the art in view of the teachings herein.

Cutter driver (430) is best seen in FIG. 20. As will be described in greater detail below, cutter driver (430) engages with both rotation assembly (420) and translation assembly (450) to manipulate cutter (30) during a biopsy procedure. Cutter driver (430) is generally overmolded or otherwise fixedly secured to cutter (30). To engage rotation assembly (420), cutter driver (430) includes a rotation portion (432). Rotation portion (432) defines a generally hexagonal cross-sectional shape that corresponds to the hexagonal shape of bore (426) in keyed actuator (424). Rotation portion (432) generally extends for a length that corresponds to the range of translation of cutter (30). In some examples, this range of motion generally corresponds to the length of lateral aperture (24), although other suitable ranges of motion can be used.

As will be described in greater detail below, cutter driver (430) is also configured to engage at least a portion of translation assembly (450). To permit this engagement, cutter driver (430) includes translation portion (434) disposed distally of rotation portion (432). Translation portion (434) includes threading (436) disposed proximally of a zero-pitch region (438). Threading (436) is generally configured to mesh with corresponding components of translation assembly (450) as will be described in greater detail below. In some examples, zero pitch region (438) can be used to provide at least some rotation of cutter (30) without corresponding translation of cutter (30).

FIG. 20 shows translation assembly (450) in greater detail. As can be seen, translation assembly (450) is generally configured as a shifting bevel gear system and includes a translator (452) that is configured to engage threading (436) of cutter driver (430). Translator (452) of the present example is generally configured as a nut. For instance, translator (452) includes a square-shaped gripping portion (454) and an elongate cylindrical receiver (456) with internal threading (458). Gripping portion (454) is configured for receipt in a portion of body (12). The square shape of gripping portion (454) permits body (12) to hold translator (452) in a fixed position relative to cutter (30) and cutter driver (430). Receiver (456) is configured to receive cutter driver (430) coaxially therein. As will be described in greater detail below, receipt of cutter driver (430) within receiver (456) permits internal threading (458) of receiver (456) to engage threading (436) of cutter driver (430) to thereby translate cutter driver (430) in response to rotation of cutter driver (430).

Reversal assembly (460) can be seen in FIG. 20. As can be seen, reversal assembly (460) includes a dual bevel gear (462), a distal bevel gear (468), a proximal bevel gear (470), and a translation shaft (472). Dual bevel gear (462) is configured to mesh with keyed actuator (424) and either distal bevel gear (468) or proximal bevel gear (470) to transfer rotation from driver (414) of input assembly (410) to keyed actuator (424). In particular, dual bevel gear (462) includes upper teeth (464) that are configured to mesh with keyed actuator (424). Dual bevel gear (462) further includes lower teeth (466) to mesh with either distal bevel gear (468) or proximal bevel gear (470).

Distal bevel gear (468) and proximal bevel gear (470) are both disposed on translation shaft (472). In particular, translation shaft (472) is configured to receive distal bevel gear (468) on the distal end adjacent to a distal flange (474). Similarly, translation shaft (472) is configured to receive proximal bevel gear (470) on a proximal end adjacent to a proximal flange (476). As will be described in greater detail below, distal flange (474) and proximal flange (476) are configured to manipulate distal bevel gear (468) and proximal bevel gear (470), respectively, into and out of engagement with dual bevel gear (462).

Translation shaft (472) is configured for receipt onto driver (414) of input assembly (410). When translation shaft (472) is received on driver (414), translation shaft (472) is configured to transfer rotary motion of driver (414) to distal bevel gear (468) and proximal bevel gear (470). Translation shaft (472) is also configured to translate relative to driver (414) while still communicating rotary motion. As will be described in greater detail below, this translation of translation shaft (472) is generally configured to transition distal bevel gear (468) and proximal bevel gear (470) into and out of engagement with dual bevel gear (462).

Figure 21A:
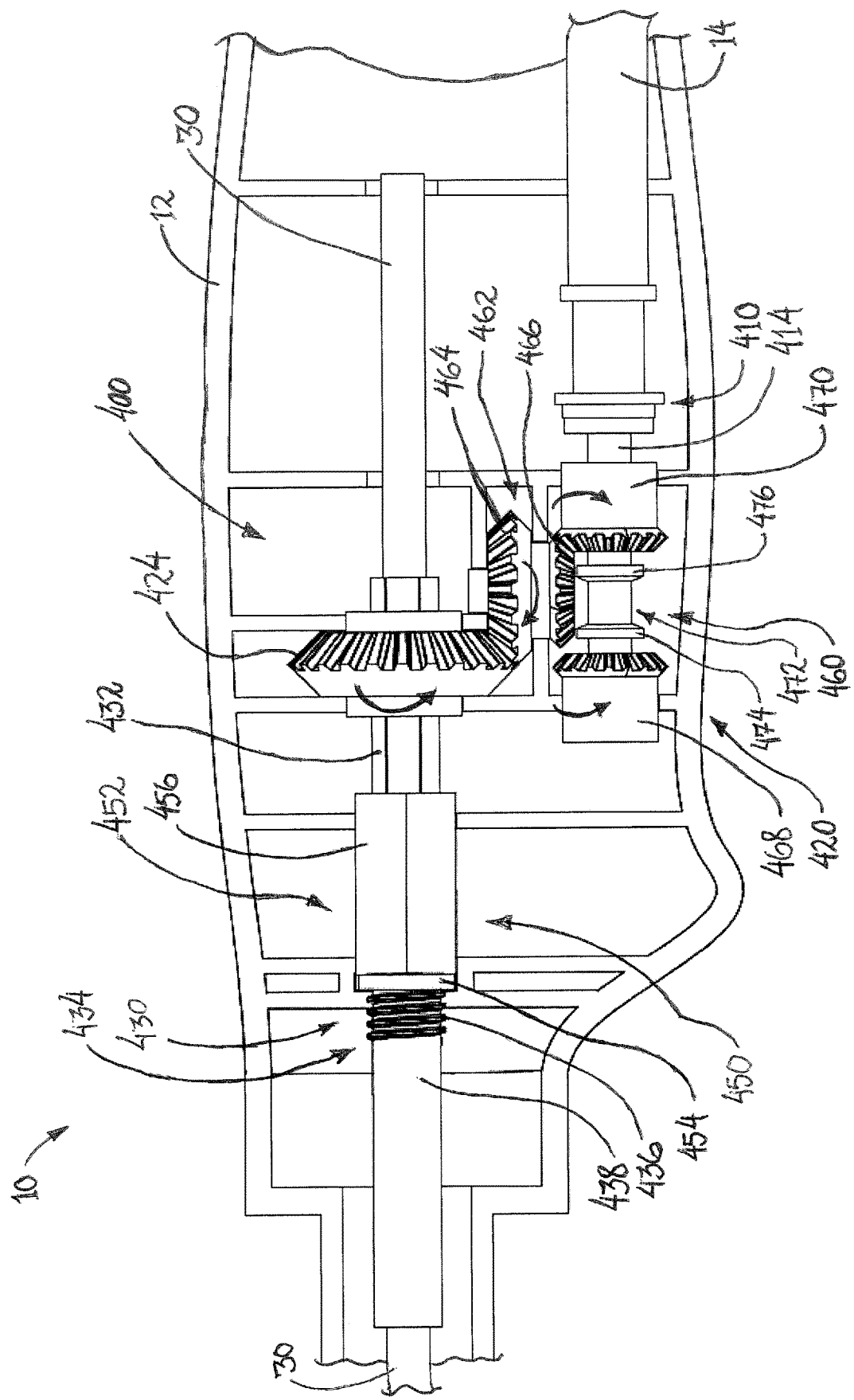
FIG. 21A depicts a side view of the cutter drive mechanism of FIG. 19, with the cutter drive mechanism in a proximal position.
Figure 21B:
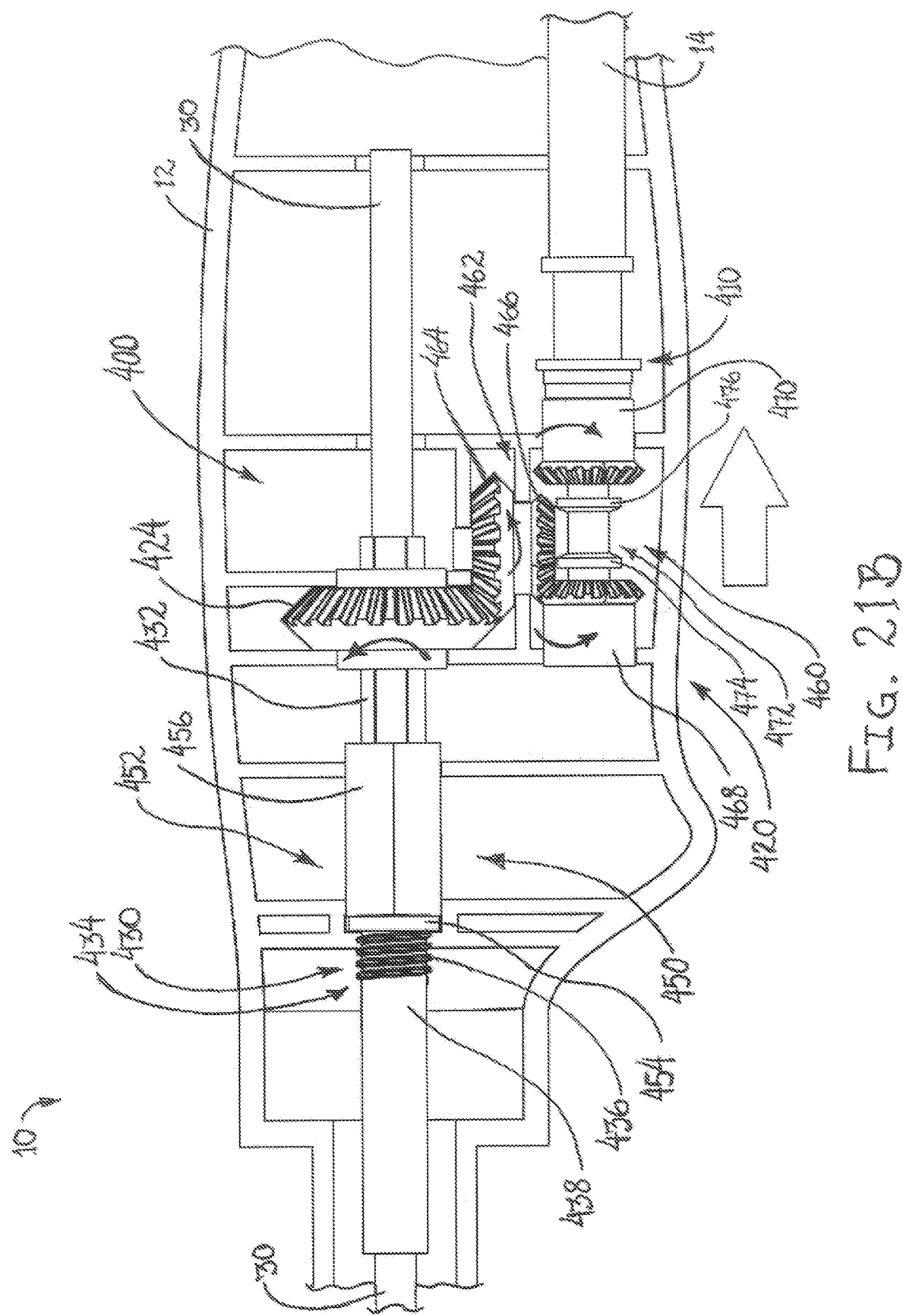
FIG. 21B depicts another side view of the cutter drive mechanism of FIG. 19, with the cutter drive mechanism in a distal position.

FIGS. 21A and 21B show an exemplary use of cutter drive mechanism (400) to provide translation of cutter (30) in two directions even when cable (14) provides a rotatory input in a single direction. As seen in FIG. 21A, one merely exemplary use can begin with reversal assembly (460) positioned such that proximal bevel gear (470) is engaged with dual bevel gear (462). In this position, clockwise (e.g., when proximal bevel gear (470) is viewed distally to proximally from the distal face of proximal bevel gear (470)) rotary motion is supplied by driver (414) of input assembly (410). Engagement between the teeth of proximal bevel gear (470) and lower teeth (466) of dual bevel gear (462) causes dual bevel gear (462) to rotate in a clockwise direction (e.g., when dual bevel gear (462) is viewed from above). Engagement between upper teeth (464) of dual bevel gear (462) with the teeth of keyed actuator (424) then causes keyed actuator (424) to rotate in a counterclockwise direction (e.g., when keyed actuator (424) is viewed distally to proximally from the distal face of keyed actuator (424)).

Rotation of keyed actuator (424) results in rotation of cutter driver (430) and cutter (30). Due to engagement between internal threading (458) of translator (452) and threading (436) of keyed actuator (424), cutter driver (430) also translates cutter (30) in response to rotation of cutter driver (430) via keyed actuator (424). The particular direction of translation is generally a function of the pitch direction of threading (436, 458). Thus, cutter drive assembly (400) can be configured to translate cutter (30) in either the distal direction or the proximal direction in response to counterclockwise rotation of keyed actuator (424). However, in the present example, cutter (30) will translate proximally due to the pitch direction of threading (436, 458). In a biopsy procedure this direction of translation can correspond to cutter (30) being retracted to open lateral aperture (24) for receipt of tissue therein.

In some circumstances it may be desirable to reverse the direction of translation of cutter (30). For instance, in the present example once cutter (30) has been retracted to fully or partially open lateral aperture, it may next be desirable to distally advance cutter (30) to sever a tissue sample. The translation direction can be reversed using reversal assembly (460) by transitioning reversal assembly (460) from the position shown in FIG. 21A to the position shown in FIG. 21B. As can be seen, translation shaft (472) is manipulated either manually or by an actuator to translate distal bevel gear (468) and proximal bevel gear (470) proximally using flanges (474, 476). This translation moves proximal bevel gear (470) out of engagement with dual bevel gear (462). Meanwhile, distal bevel gear (468) is moved into engagement with dual bevel gear (462).

Once distal bevel gear (468) is engaged with dual bevel gear (462), the teeth of distal bevel gear (468) engage lower teeth (466) of dual bevel gear (462) to drive dual bevel gear (462) in an opposite counterclockwise direction even though distal bevel gear (468) moves in the same clockwise direction as proximal bevel gear (470). Upper teeth (464) of dual bevel gear (462) then engage the teeth of keyed actuator (424) and drive keyed actuator (424) in an opposite counterclockwise direction. This opposite rotation of keyed actuator (424) causes cutter driver (430) and cutter (30) to rotate in an opposite direction. Due to engagement between internal threading (458) of translator (452) and threading (436) of keyed actuator (424), cutter driver (430) also translates cutter (30) in an opposite direction due to the opposite rotation of cutter driver (430) via keyed actuator (424).

Translation of cutter (30) can continue via the drive position shown in FIG. 21B until it is desired to again reverse the translation of cutter (30). For instance, in the present example the configuration shown in FIG. 21B will result in distal translation of cutter (30) due to the pitch angle of threading (436, 458). This distal translation can continue until, for example, cutter (30) is translated distally of lateral aperture (24) to fully sever a tissue sample and close lateral aperture (24). Cutter actuation assembly (400) can then be returned to the position shown in FIG. 21A to again translate cutter (30) proximally without reversing the direction of rotary input provided by driver (414) of input assembly (410).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes, It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device, the biopsy device comprising: (a) a body; (b) a needle extending distally from the body; (c) a cutter movable relative to the needle to sever a tissue sample; and (d) a cutter drive mechanism driven by a rotary drive cable and configured to both rotate and translate the cutter, wherein the cutter drive mechanism is configured to reverse the translation direction of the cutter while the drive provided by the rotary drive cable is in a continuous rotary direction.

Example 2

The biopsy device of Example 1, wherein the cutter drive mechanism is configured to drive translation of the cutter at a non-linear rate.

Example 3

The biopsy device of Example 2, wherein the non-linear rate defines a sinusoidal pattern as a function of axial displacement.

Example 4

The biopsy device of any one or more of Examples 1 through 3, wherein the cutter drive mechanism is configured to rotate the cutter at a constant angular velocity.

Example 5

The biopsy device of any one or more of Examples 1 through 4, wherein the cutter drive mechanism includes a translation assembly having a translator wheel mechanically coupled to the cutter by an elongate connector, wherein the elongate connector is configured to drive translation of the cutter in response to rotation of the translator wheel.

Example 6

The biopsy device of Example 5, wherein the cutter drive mechanism further includes a cutter driver having a translation portion and a rotation portion, wherein the translation portion is configured to couple to the connector by a coupler fastened to the translation portion.

Example 7

The biopsy device of any one or more of Examples 5 through 6, wherein the connector is configured to pivot relative to the translator wheel on a translation post.

Example 8

The biopsy device of any one or more of Examples 5 through 7, wherein the cutter drive mechanism further includes a worm gear in mechanical communication with the translator wheel, wherein the worm gear is configured to rotate the translator wheel in response to rotation of the rotary drive cable.

Example 9

The biopsy device of any one or more of Examples 5 through 8, wherein the cutter drive mechanism further includes a rotation assembly having a keyed actuator, wherein the keyed actuator is coaxial with the cutter and is configured to rotate the cutter while permitting translation of the cutter relative to the keyed actuator.

Example 10

The biopsy device of Example 9, wherein the keyed actuator defines a bore having a hexagonal shape.

Example 11

A biopsy device, the biopsy device comprising: (a) a body; (h) a needle extending distally from the body; (c) a cutter movable relative to the needle to sever a tissue sample; (d) a rotary drive cable configured to transmit rotary motion to the body; and (e) a cutter drive mechanism configured to convert the rotary motion of the rotary drive cable into rotation and translation of the cutter, wherein the cutter drive mechanism is configured to translate the cutter distally and proximally in response to the rotary motion provided by the rotary drive cable being in a single angular direction.

Example 12

The biopsy device of Example 11, wherein the cuter drive mechanism includes a cutter rotation assembly and a cutter translation assembly, wherein the cutter rotation assembly is configured to rotate the cutter continuously in response to the rotary motion provided by the rotary drive cable, wherein the cutter translation assembly is configured to automatically transition between translating the cutter distally and translating the cutter proximally.

Example 13

The biopsy device of Example 11, wherein the cuter drive mechanism includes a cutter rotation assembly and a cutter translation assembly, wherein the cutter rotation assembly is configured to rotate the cutter continuously in response to the rotary motion provided by the rotary drive cable, wherein the cutter translation assembly is configured to selectively transition between translating the cutter distally and translating the cutter proximally while the rotary on provided by the rotary drive cable is in a single continuous angular direction.

Example 14

The biopsy device of Example 11, wherein the cutter drive mechanism includes a rotatable translator having threading, wherein the threading defines dual drive paths.

Example 15

The biopsy device of Example 11, wherein the cutter drive mechanism includes a rotatable translator having threading and a traveler configured to engage the threading, wherein the threading defines dual drive paths, wherein the traveler is configured to translate the cutter in response to rotation of the translator.

Example 16

The biopsy device of Example 11, wherein the cutter drive mechanism includes a rotatable translator having threading and a traveler configured to engage the threading, wherein the threading defines dual drive paths, wherein the traveler is configured to translate the cutter in response to rotation of the translator, wherein at least a portion of the translator is rotatable relative to the cutter to permit the translator to transition from a first drive path to a second drive path defined by the threading of the translator.

Example 17

The biopsy device of Example 11, wherein the cutter drive mechanism includes a rotatable translator having threading and a traveler configured to engage the threading, wherein the threading defines dual drive paths, wherein the traveler is configured to translate the cutter in response to rotation of the translator, wherein at least a portion of the translator is rotatable relative to the cutter to permit the translator to transition from a first drive path to a second drive path defined by the threading of the translator, wherein the first drive path and the second drive path are connected by a reversal portion.

Example 18

The biopsy device of any one or more of Examples 11 through 17, further comprising an input assembly, wherein the input assembly is configured to communicate the rotary motion from the rotary drive cable to the cutter drive mechanism.

Example 19

The biopsy device of any one or more of Examples 11 through 18, wherein the rotary drive cable is detachable from the body.

Example 20

The biopsy device of Example 11, wherein the cutter drive mechanism includes a rotatable translator having threading and a traveler configured to engage the threading, wherein the threading defines dual drive paths, wherein the traveler is configured to translate the cutter in response to rotation of the translator, wherein the translator is greater than the length of a lateral aperture defined by the needle.

Example 21

A cutter drive mechanism for use in a biopsy device powered by a rotary drive cable, the cutter drive mechanism comprising: a translation mechanism and a rotation mechanism, wherein both the translation mechanism and the rotation mechanism are in communication with the rotary drive cable to translate and rotate a cutter of the biopsy device, wherein the translation mechanism is configured to translate the cutter distally and proximally in response to rotation of a portion of the rotary drive cable in a single angular direction.

Example 22

The biopsy device of Example 21, wherein the cutter drive mechanism further includes a translation assembly having a translator wheel mechanically coupled to the cutter by an elongate connector, wherein the elongate connector is configured to drive translation of the cutter in response to rotation of the translator wheel.

Example 23

The biopsy device of Example 22, wherein the cutter drive mechanism further includes a cutter driver having a translation portion and a rotation portion, wherein the translation portion is configured to couple to the connector by a coupler fastened to the translation portion.

Example 24

The biopsy device of any one or more of Examples 22 through 23, wherein the connector is configured to pivot relative to the translator wheel on a translation post.

Example 25

The biopsy device of any one or more of Examples 22 through 24, wherein the cutter drive mechanism further includes a worm gear in mechanical communication with the translator wheel, wherein the worm gear is configured to rotate the translator wheel in response to rotation of the rotary drive cable.

Example 26

A method of using a biopsy device, wherein the method comprises: rotating an input assembly of a cutter drive mechanism disposed within a body of the biopsy device by rotating rotary drive cable in a first angular direction; retracting a cutter of the biopsy device proximally to open a lateral aperture of a needle associated with the cutter using the cutter drive mechanism while continuing to rotate the rotary drive cable in the first angular direction; and advancing the cutter distally relative to the lateral aperture to sever a tissue sample using the cutter drive mechanism while continuing to rotate the rotary drive cable in the first angular direction.

Example 27

The method of Example 26, further including rotating the cutter continuously using the cutter drive mechanism by rotating the rotary drive cable in the first angular direction.

Example 28

The biopsy device of Example 27, wherein the step of rotating the cutter is performed simultaneously with the steps of retracting the cutter and advancing the cutter.

Example 29

The biopsy device of any one or more of Examples 26 through 28, further including actuating a portion of the cutter drive mechanism to transition from the step of retracting the cutter to the step of advancing the cutter.

Example 30

The biopsy device of any one or more of Examples 26 through 29, wherein the step of retracting the cutter is repeated after the step of advancing the cutter.

Example 31

A biopsy device, the biopsy device comprising: (a) a body; (b) a needle extending distally from the body; (c) a cutter movable relative to the needle to sever a tissue sample; (d) a rotary drive cable configured to transmit rotary motion to the body; and (e) a cutter drive mechanism including a translation assembly, a rotation assembly, and a reversal assembly, wherein the rotation assembly includes a keyed actuator configured to rotate the cutter, wherein the translation assembly includes a translator configured to translate the cutter in response to rotation of the cutter, wherein the reversal assembly is in communication with the rotary drive cable and includes one or more gears configured to move relative to the keyed actuator to reverse the direction of rotation of the keyed actuator without reversing the direction of rotation of the rotary drive cable.

Example 32

The biopsy device of Example 31, wherein the reversal assembly includes a housing configured to enclose the one or more gears of the reversal assembly, wherein the housing is movable relative to keyed actuator to reverse the direction of rotation of the keyed actuator.

Example 33

The biopsy device of Example 32, wherein the one or more gears of the reversal assembly includes with a first stage rotation gear, a second stage rotation gear, and a reversal gear disposed within the housing, wherein the first stage rotation gear is configured to drive the keyed actuator in a first direction, wherein the second stage rotation gear and the reversal gear are configured to drive the keyed actuator in a second direction.

Example 34

The biopsy device of Example 31, wherein the one or more gears of the reversal assembly incudes a first bevel gear, a second bevel gear, and a dual bevel gear, wherein the dual bevel gear is configured to communicate rotary motion from the first bevel gear or the second bevel gear to the keyed actuator, wherein the first bevel gear and second bevel gear are both configured to rotate in response to rotation of the rotary drive cable, wherein the first bevel gear and the second bevel gear are both configured to selectively move relative to the dual bevel gear to independently communicate rotary motion to the dual bevel gear.

Example 35

The biopsy device of any one or more of Examples 31 through 34, wherein the translator includes a nut, wherein the nut includes internal threading configured to engage external threading associated with the cutter to translate the cutter in response to rotation of the cutter.

Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, the biopsy device comprising:
   (a) a body;
   (b) a needle extending distally from the body;
   (c) a cutter movable relative to the needle to sever a tissue sample; and
   (d) a cutter drive mechanism driven by a rotary drive cable and configured to both rotate and translate the cutter,
   the cutter drive mechanism including a translation assembly having a translator wheel mechanically coupled to the cutter by an elongate connector, the elongate connector being configured to drive translation of the cutter in response to rotation of the translator wheel, and
   the cutter drive mechanism further including a worm gear in mechanical communication with the translator wheel, the worm gear being configured to rotate the translator wheel in response to rotation of the rotary drive cable to translate the cutter using the elongate connector, and
   the translation assembly being configured to drive the cutter in both distal and proximal directions sequentially while drive provided by the worm gear via the rotary drive cable is in a continuous rotary direction.

2. The biopsy device of claim 1, the cutter drive mechanism being configured to drive the translation of the cutter at a non-linear rate.

3. The biopsy device of claim 2, the non-linear rate defining a sinusoidal pattern as a function of axial displacement.

4. The biopsy device of claim 1, the cutter drive mechanism being configured to rotate the cutter at a constant angular velocity.

5. The biopsy device of claim 1, the cutter drive mechanism further including a cutter driver having a translation portion and a rotation portion, the translation portion being configured to couple to the connector by a coupler fastened to the translation portion.

6. The biopsy device of claim 1, the connector being configured to pivot relative to the translator wheel on a translation post.

7. The biopsy device of claim 1, the cutter drive mechanism further including a cutter driver having a translation portion and a rotation portion, the translation portion being configured to couple to the connector by a coupler fastened to the translation portion, the connector being configured to pivot relative to the translator wheel on a translation post.

8. The biopsy device of claim 1, the cutter drive mechanism further including a rotation assembly having a keyed actuator, the keyed actuator being coaxial with the cutter and being configured to rotate the cutter while permitting the translation of the cutter relative to the keyed actuator.

9. The biopsy device of claim 8, the keyed actuator defining a bore having a hexagonal shape.

10. The biopsy device of claim 1, the body being configured to detachably couple to the rotary drive cable.

11. A biopsy device comprising:
    (a) a body;
    (b) a needle extending distally from the body, the needle defining a lateral aperture;
    (c) a cutter movable relative to the needle to sever a tissue sample;
    (d) a rotary drive cable configured to transmit rotary motion to the body; and
    (e) a cutter drive mechanism configured to convert the rotary motion of the rotary drive cable into rotation and translation of the cutter, the cutter drive mechanism being configured to translate the cutter distally and proximally in response to the rotary motion provided by the rotary drive cable being in a single angular direction,
    the cutter drive mechanism including a translation assembly having a translator wheel mechanically coupled to the cutter by an elongate connector, the elongate connector being configured to drive the translation of the cutter in response to rotation of the translator wheel,
    the translator wheel defining a translator diameter, the translator diameter corresponding to an axial length of the lateral aperture of the needle.

12. The biopsy device of claim 11, the cutter drive mechanism further including a cutter rotation assembly, the cutter rotation assembly being configured to rotate the cutter continuously in response to the rotary motion provided by the rotary drive cable, the translation assembly being configured to automatically transition between translating the cutter distally and translating the cutter proximally.

13. A method of using a biopsy device, wherein the method comprises:
    rotating a translator of an input assembly of a cutter drive mechanism disposed within a body of the biopsy device by rotating a rotary drive cable in a first angular direction;
    retracting a cutter of the biopsy device proximally to open a lateral aperture of a needle associated with the cutter using the cutter drive mechanism while continuing to rotate the rotary drive cable in the first angular direction; and
    advancing the cutter distally relative to the lateral aperture to sever a tissue sample using the cutter drive mechanism to close the lateral aperture of the needle while continuing to rotate the rotary drive cable in the first angular direction
    the steps of retracting the cutter and advancing the cutter being performed with the translator rotating a single rotation to translate the cutter from a distal position to a proximal position and back to the distal position.

* * * * *